(12) United States Patent
Makrigiorgos

(10) Patent No.: US 11,174,511 B2
(45) Date of Patent: Nov. 16, 2021

(54) METHODS AND COMPOSITIONS FOR SELECTING AND AMPLIFYING DNA TARGETS IN A SINGLE REACTION MIXTURE

(71) Applicant: Dana-Farber Cancer Institute, Inc., Boston, MA (US)

(72) Inventor: Gerassimos Makrigiorgos, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/633,763

(22) PCT Filed: Jul. 24, 2018

(86) PCT No.: PCT/US2018/043506
§ 371 (c)(1),
(2) Date: Jan. 24, 2020

(87) PCT Pub. No.: WO2019/023243
PCT Pub. Date: Jan. 31, 2019

(65) Prior Publication Data
US 2020/0370108 A1 Nov. 26, 2020

Related U.S. Application Data

(60) Provisional application No. 62/536,187, filed on Jul. 24, 2017.

(51) Int. Cl.
*C12Q 1/68* (2018.01)
*C12Q 1/6848* (2018.01)

(52) U.S. Cl.
CPC .................. *C12Q 1/6848* (2013.01)

(58) Field of Classification Search
CPC ........................................................ C12Q 1/68
(Continued)

(56) References Cited

U.S. PATENT DOCUMENTS

| 4,458,066 A | 7/1984 | Caruthers et al. |
| 4,683,195 A | 7/1987 | Mullis et al. |

(Continued)

FOREIGN PATENT DOCUMENTS

| CN | 1650028 A | 8/2005 |
| EP | 0 370 719 A2 | 5/1990 |

(Continued)

OTHER PUBLICATIONS

Gholami et al., A tailed PCR procedure for cost-effective, two-order multiplex sequencing of candidate genes in polyploid plants, Plant Biotechnol J. Aug. 2012;10(6):635-45. doi: 10.1111/j.1467-7652.2012.00696.x. Epub Apr. 11, 2012.*

(Continued)

*Primary Examiner* — Aaron A Priest
(74) *Attorney, Agent, or Firm* — Wolf, Greenfield & Sacks, P.C.

(57) ABSTRACT

This disclosure relates to compositions and methods for single-step, multi-stage amplification reactions that combine many stages of sample preparation process in a single tube reaction. The disclosed technology provides a mean of performing multiplexed nested PCR in a single vessel, without any need of purification steps, and is based on the use of three sets of primers: a pair of outer primers, a pair of inner primers that are nested within the pair of outer primers, and tail primers that are complementary to tails on the inner primers. By adjusting the temperature conditions, annealing temperatures of the primers, number of amplifi- (Continued)

cation cycles, and the concentrations of the outer, inner, and tail primers, it is possible to carry out multiplexed nested PCR in a single vessel.

17 Claims, 10 Drawing Sheets

(58) Field of Classification Search
USPC .......................................................... 435/6.12
See application file for complete search history.

(56) References Cited

U.S. PATENT DOCUMENTS

| | | |
|---|---|---|
| 4,683,202 A | 7/1987 | Mullis |
| 4,800,159 A | 1/1989 | Mullis et al. |
| 5,045,450 A | 9/1991 | Thilly et al. |
| 5,075,217 A | 12/1991 | Weber |
| 5,256,775 A | 10/1993 | Froehler |
| 5,399,491 A | 3/1995 | Kacian et al. |
| 5,409,818 A | 4/1995 | Davey et al. |
| 5,427,930 A | 6/1995 | Birkenmeyer et al. |
| 5,541,308 A | 7/1996 | Hogan et al. |
| 5,554,527 A | 9/1996 | Fickenscher |
| 5,565,340 A | 10/1996 | Chenchik et al. |
| 5,612,473 A | 3/1997 | Wu et al. |
| 5,618,703 A | 4/1997 | Gelfand et al. |
| 5,631,147 A | 5/1997 | Lohman et al. |
| 5,648,211 A | 7/1997 | Fraiser et al. |
| 5,744,311 A | 4/1998 | Fraiser et al. |
| 5,792,607 A | 8/1998 | Backman et al. |
| 5,846,710 A | 12/1998 | Bajaj |
| 5,849,497 A | 12/1998 | Steinman |
| 5,994,056 A | 11/1999 | Higuchi |
| 6,030,115 A | 2/2000 | Ishiguro et al. |
| 6,174,680 B1 | 1/2001 | Makrigiorgos |
| 6,197,499 B1 | 3/2001 | Hughes et al. |
| 7,435,794 B2 | 10/2008 | Lukyanov et al. |
| 7,618,773 B2 | 11/2009 | Rand et al. |
| 7,635,566 B2 | 12/2009 | Brenner |
| 8,071,338 B2 | 12/2011 | Newton |
| 8,268,564 B2 | 9/2012 | Roth et al. |
| 8,440,404 B2 | 5/2013 | Makarov et al. |
| 8,455,190 B2 | 6/2013 | Makrigiorgos |
| 8,623,603 B2 | 1/2014 | Makrigiorgos |
| 8,628,924 B2 | 1/2014 | Kacian et al. |
| 8,691,509 B2 * | 4/2014 | May .................. C12Q 1/686 435/6.12 |
| 8,455,190 C1 | 9/2015 | Makrigiorgos |
| 9,133,490 B2 | 9/2015 | Candau-Chacon |
| 9,957,556 B2 | 5/2018 | Makrigiorgos |
| 2002/0016680 A1 | 2/2002 | Wang et al. |
| 2002/0045227 A1 | 4/2002 | Wagener |
| 2003/0008286 A1 | 1/2003 | Zou et al. |
| 2003/0092021 A1 | 5/2003 | Thilly |
| 2004/0023207 A1 | 2/2004 | Polansky |
| 2004/0033518 A1 | 2/2004 | Wittwer et al. |
| 2004/0166519 A1 | 8/2004 | Cargill et al. |
| 2005/0089984 A1 | 4/2005 | Ginns et al. |
| 2005/0175996 A1 | 8/2005 | Chen |
| 2005/0266417 A1 | 12/2005 | Barany et al. |
| 2006/0063175 A1 | 3/2006 | Xu et al. |
| 2006/0263789 A1 | 11/2006 | Kincaid |
| 2007/0020672 A1 | 1/2007 | Wittwer et al. |
| 2007/0154892 A1 | 7/2007 | Wain-Hobson et al. |
| 2008/0254453 A1 | 10/2008 | Shapero et al. |
| 2008/0269068 A1 | 10/2008 | Church et al. |
| 2009/0068652 A1 | 3/2009 | Taylor et al. |
| 2009/0148842 A1 | 6/2009 | Gormley |
| 2010/0173311 A1 | 7/2010 | Grow et al. |
| 2010/0184153 A1 | 7/2010 | Brookes |
| 2010/0203532 A1 | 8/2010 | Makrigiorgos |
| 2010/0233683 A1 | 9/2010 | Molloy et al. |
| 2011/0217714 A1 | 9/2011 | Makrigiorgos |
| 2012/0220494 A1 | 8/2012 | Samuels et al. |
| 2012/0225421 A1 | 9/2012 | Richardson et al. |
| 2013/0059734 A1 | 3/2013 | Molloy et al. |
| 2013/0303385 A1 | 11/2013 | Korlach et al. |
| 2013/0309724 A1 | 11/2013 | Candau-Cachon |
| 2014/0051087 A1 | 2/2014 | Makrigiorgos |
| 2014/0106362 A1 | 4/2014 | Makrigiorgos |
| 2014/0315726 A1 | 10/2014 | Beatty et al. |
| 2015/0247182 A1 | 9/2015 | Faham et al. |
| 2016/0046986 A1 | 2/2016 | Eltoukhy et al. |
| 2016/0186237 A1 | 6/2016 | Makrigiorgos et al. |
| 2016/0289670 A1 | 10/2016 | Samuels et al. |
| 2016/0369333 A1 | 12/2016 | Babiarz et al. |
| 2017/0130258 A1 | 5/2017 | Sampas |
| 2018/0187242 A1 | 7/2018 | Makrigiorgos et al. |
| 2018/0282798 A1 | 10/2018 | Makrigiorgos |

FOREIGN PATENT DOCUMENTS

| | | |
|---|---|---|
| EP | 2 004 852 B1 | 12/2010 |
| GB | 2 293 238 A | 3/1996 |
| WO | WO 1990/11369 A1 | 10/1990 |
| WO | WO 1990/13668 A1 | 11/1990 |
| WO | WO 1991/14003 A2 | 9/1991 |
| WO | WO 1997/19193 A2 | 5/1997 |
| WO | WO 1999/14226 A2 | 3/1999 |
| WO | WO 1999/61661 A1 | 12/1999 |
| WO | WO 2001/068900 A2 | 9/2001 |
| WO | WO 2002/018659 A2 | 3/2002 |
| WO | WO 2002/086155 A2 | 10/2002 |
| WO | WO 2003/072809 A1 | 9/2003 |
| WO | WO 2005/093101 A1 | 10/2005 |
| WO | WO 2007/047572 A2 | 4/2007 |
| WO | WO 2007/106534 A2 | 9/2007 |
| WO | WO 2009/017784 A2 | 2/2009 |
| WO | WO 2009/019008 A1 | 2/2009 |
| WO | WO 2010/065626 A1 | 6/2010 |
| WO | WO 2011/112534 A1 | 9/2011 |
| WO | WO 2012/135664 A2 | 10/2012 |
| WO | WO 2015/013166 A1 | 1/2015 |
| WO | WO 2016/210224 | 12/2016 |

OTHER PUBLICATIONS

Fadrosh et al., An improved dual-indexing approach for multiplexed 16S rRNA gene sequencing on the Illumina MiSeq platform, Microbiome. Feb. 24, 2014;2(1):6. doi: 10.1186/2049-2618-2-6.*
International Search Report and Written Opinion for PCT/US2020/047098, dated Feb. 2, 2021.
Invitation to Pay Additional Fees for PCT/US2020/047098, dated Nov. 9, 2020.
Ladas et al. Multiplexed Elimination of Wild-Type DNA and High-Resolution Melting Prior to Targeted Resequencing of Liquid Biopsies. Clin Chem. 2017;63(10):1605-1613. doi: 10.1373/clinchem. 2017.272849.
Owczarzy et al., Predicting stability of DNA duplexes in solutions containing magnesium and monovalent cations. Biochemistry. May 13, 2008;47(19):5336-53. doi: 10.1021/bi702363u. Epub Apr. 19, 2008.
U.S. Appl. No. 16/469,057, filed Jun. 12, 2019, Makrigiorgos et al.
U.S. Appl. No. 90/013,365, filed Oct. 15, 2014, Makrigiorgos.
EP12764286.6, Nov. 17, 2014, Partial Supplementary European Search Report.
EP12764286.6, Mar. 18, 2015, Extended European Search Report.
EP 17196718.5, May 14, 2018, Extended European Search Report.
PCT/US2012/031527, Aug. 28, 2012, Invitation to Pay Additional Fees.
PCT/US2012/031527, Nov. 5, 2012, International Search Report and Written Opinion.
PCT/US2012/031527, Oct. 10, 2013, International Preliminary Report on Patentability.
PCT/US2014/047373, Nov. 12, 2014, International Search Report and Written Opinion.
PCT/US2014/047373, Feb. 4, 2016, International Preliminary Report on Patentability.
16815352.6, Oct. 16, 2018, Extended European Search Report.

(56) References Cited

OTHER PUBLICATIONS

PCT/US2016/039167, Sep. 26, 2016, International Search Report and Written Opinion.
PCT/US2016/039167, Dec. 26, 2017, International Preliminary Report on Patentability.
PCT/US2017/065747, Jun. 27, 2019, International Preliminary Report on Patentability.
PCT/US2017/065747, Mar. 6, 2018, International Search Report and Written Opinion.
PCT/US2011/027473, Jun. 28, 2011, International Search Report and Written Opinion.
PCT/US2011/027473, Sep. 20, 2012, International Preliminary Report on Patentability.
PCT/US2018/043506, Oct. 9, 2018, International Search Report and Written Opinion.
[No Author Listed] BioMath Calculators: Tm Calculation for Oligos. Last accessed Oct. 27, 2014 from https://www.promega.com/techserv/tools/biomath/calc11.htm.
[No Author Listed] Cold-PCR: Very High Sensitivity Mutation Detection. Transgenomic. Jul. 1, 2010: 31 pages. Last accessed at <http://www.transgenomic.com/files/literature/48227300.pdf> on Oct. 25, 2014.
[No Author Listed] Integrated DNA Technologies: Molecular Facts and Figures [online] [retrieved on Feb. 17, 2015] retrieved from https://www.idtdna.com/pages/docs/educational-resources/molecular-facts-and-figures.pdf?sfvrsn=4.
[No Author Listed] User Guide for the Reveal Kit KRAS Exon 2. A Mutation Enrichment Assay Powered by Ice Cold-PCR. Transgenomic, Inc 2012.
[No Author Listed], "Paired-End Sequencing Sample Preparation Guide," Illumina Catalog #PE-930-1001, Sep. 1, 2009 (Sep. 1, 2009), pp. 1-34. Retrieved from the Internet: <http://mmjggl.caltech.edu/sequencing/Paired-End_SamplePrep_ Guide_ 1005063_8.pdf> on Feb. 1, 2018 (Feb. 1, 2018). entire document.
Adalsteinsosn: Recent literature: listed in http://personal.broadinstitute.org/viktor/publications.html. 2016.
Ahmadian et al., Pyrosequencing: history, biochemistry and future. Clin Chim Acta. Jan. 2006;363(1-2):83-94. Epub Sep. 13, 2005.
Ahrendt et al., p53 mutations and survival in stage I non-small-cell lung cancer: results of a prospective study. J Natl Cancer Inst. Jul. 2, 2003;95(13):961-70.
Alix-Panabières et al., Clinical Applications of Circulating Tumor Cells and Circulating Tumor DNA as Liquid Biopsy. Cancer Discov. May 2016; 6(5):479-91. doi: 10.1158/2159-8290.CD-15-1483. Epub Mar. 11, 2016.
Altschul et al., Gapped Blast and PSI-Blast: a new generation of protein database search programs. Nucleic Acids Res. Sep. 1, 1997;25(17):3389-402.
Amicarelli et al., Flag assay as a novel method for real-time signal generation during PCR: application to detection and genotyping of KRAS codon 12 mutations. Nucleic Acids Res. 2007;35(19):e131. Epub Oct. 11, 2007.
Aoki et al., Liposome-mediated in vivo gene transfer of antisense K-ras construct inhibits pancreatic tumor dissemination in the murine peritoneal activity. Cancer Res. Sep. 1, 1995;55(17):3810-6.
Armour et al., Recent advances in minisatellite biology. FEBS Lett. Jul. 27, 1992;307(1):113-5.
Bansal et al., Statistical analysis strategies for association studies involving rare variants. Nat Rev Genet. Nov. 2010; 11(11):773-85. doi: 10.1038/nrg2867. Epub Oct. 13, 2010.
Beaucage et al., Deoxynucleoside phosphoramidites—A new class of key intermediates for deoxypolynucleotide synthesis. Tetrahedron Letters. 1981;22(20):1859-62. doi:10.1016/S00404039(01)90461-7.
Beau-Faller et al., Detection of K-Ras mutations in tumur samples of patients with non-small cell lung cancer using PNA-mediated PCR clamping. Br J Cancer. Mar. 24, 2009;100(6):985-92. doi:10.1038/sj.bjc.6604925.
Behn et al., Simple and reliabe factor V genotyping by PNA-mediated PCR clamping. Thromb Haemost. Apr. 1998;79(4):773-7.
Belinsky et al., Gene promoter methylation in plasma and sputum increases with lung cancer risk. Clin Cancer Res. Sep. 15, 2005;11(18):6505-11.
Bettegowda et al., Detection of circulating tumor DNA in early- and late-stage human malignancies. Sci Transl Med. Feb. 19, 2014; 6(224):224ra24. doi: 10.1126/scitranslmed.3007094.
Bi et al., Detection of known mutation by proof-reading PCR. Nucleic Acids Res. Jun. 15, 1998;26(12):3073-5.
Bidard et al., Going with the flow: from circulating tumor cells to DNA. Sci Transl Med. Oct. 16, 2013; 5(207):207ps14. doi: 10.1126/scitranslmed.3006305.
Blake et al., Thermal stability of DNA. Nucleic Acids Res. Jul. 15, 1998;26(14):3323-32.
Boisselier et al., Cold PCR HRM: a highly sensitive detection method for IDH1 mutations. Hum Mutat. Dec. 2010;31(12):1360-5. doi: 10.1002/humu.21365. Epub Nov. 9, 2010.
Botstein et al., Construction of a genetic linkage map in man using restriction fragment length polymopishms. Am J Hum Genet. May 1980;32(3):314-31.
Braasch et al., Locked nucleic acid (LNA): fine-tuning the recognition of DNA and RNA. Chem Biol. Jan. 2001;8(1):1-7.
Bunyan et al., Different denaturation rates between methylated and non-methylated genomic DNA can result in allele-specific PCR amplification. Open J. Gen. Sep. 2011;1:13-14.
Candau et al., Very High Sensitivity Detection of K-RAS Exon 2 Mutations Using Fast Cold-PCR. AACR 2010 Poster Presentation.
Castellanos-Rizaldos et al., Cold-PCR amplification of bisulfire-converted DNA allows the enrichment and sequencing of rare un-methylated genomic regions. PLoS One. Apr. 11, 2014; 9(4):e94103. doi: 10.1371/journal.pone.0094103. eCollection 2014.
Castellanos-Rizaldos et al., Enhanced ration of signals enables digital mutation scanning for rare allele detection. J Mol Diagn. May 2015; 17(3):284-92. doi: 10.1016/j.jmoldx.2014.12.003. Epub Mar. 13, 2015.
Castellanos-Rizaldos et al., Enrichment of mutations in multiple DNA sequences using Cold-PCR in emulsion. PLoS One. 2012; 7(12):e51362. doi: 10.1371/journal.pone.0051362. Epub Dec. 6, 2012.
Castellanos-Rizaldos et al., Single-tube, highly parallel mutation enrichment in cancer gene panels by use of temperature-tolerant Cold-PCR. Clin Chem. Jan. 2015; 61(1):267-77. doi: 10.1373/clinchem.2014.228361. Epub Oct. 8, 2014.
Castellanos-Rizaldos et al., Temperature-tolerant Cold-PCR reduces temperature stringency and enables robust mutation enrichment. Clin Chem. Jul. 2012;58(7):1130-8. doi: 10.1373/clinchem.2012.183095. Epub May 15, 2012.
Chakrabarti et al., Highly selective isolation of unknown mutations in diverse DNA fragments: toward new multiplex screening in cancer. Cancer Res. Jul. 15, 2000;60(14):3732-7.
Chan et al., Noninvasive detection of cancer-associated genome-wide hypomethylation and copy number aberrations by plasma DNA bisulfite sequencing. Proc Natl Acad Sci U S A. Nov. 19, 2013; 110(47):18761-8. doi: 10.1073/pnas.131995110. Epub Nov. 4, 2013.
Chen et al., Fetal DNA analyzed in plasma from a mother's three consecutive pregnancies to detect paternally inherited aneuploidy. Clin Chem. May 2001;47(5):937-9.
Chiu et al., Hypermethylation of RASSFIA in human and rhesus placentas. Am J Pathol. Mar. 2007;170(3):941-50.
Chou et al., A comparison of high-resolution melting analysis with denaturing high-performance liquid chromatography for mutation scanning: cystic fibrosis transmembrane conductance regulator gene as a model. Am J Clin Pathol. Sep. 2005;124(3):330-8.
Chow et al., Mass spectrometric detection of an SNP panel as an internal positive control for fetal DNA analysis in maternal plasma. Clin Chem. Jan. 2007;53(1):141-2.
Compton, Nucleic acid sequence-based amplification. Nature. Mar. 7, 1991;350(6313):91-2.
Corless et al., Allele-specific polymerase chain reaction for the imatinib-resistant Kit D816V and D816F mutations in mastocytosis and acute myelogenous leukemia. J Mol Diag Nov. 2006;8(5):604-612.
Coutelle, New DNA-analysis techniques (minireview). Biomed Biochim Acta. 1991;50(1):3-10.

(56) References Cited

OTHER PUBLICATIONS

Cullen et al., Thermal denaturation of DNA from bromodeoxyuridine substituted cells. Nucleic Acids Res. Jan. 1976; 3(1):49-62.

Däbritz et al., Detection of Ki-ras mutations in tissue and plasma samples of patients with pancreatic cancer using PNA-mediated PCR clamping and hybridisation probes. Br J Cancer. Jan. 31, 2005;92(2):405-12.

Dawson et al., Analysis of circulating tumor DNA to monitor metastatic brease cancer. N Engl J Med. Mar. 28, 2013; 368(13):1199-209. doi: 10.1056/NEJMoa1213261. Epub Mar. 13, 2013.

Delaney et al., GNAS1 mutations occur more commonly than previously thought in intramuscular myxoma. Mod. Pathol. May 2009;22(5):718-24. doi: 10.1038/modpathol.2009.32. Epub Mar. 13, 2009.

Di Fiore et al., Clinical relevance of KRAS mutation detection in metastatic colorectal cancer treated by Cetuximab plus chemotherapy. Br J Cancer. Apr. 23, 2007;96(8):1166-9. Epub Mar. 20, 2007.

Diaz et al., Liquid biopsies: genotyping circulating tumor DNA. J Clin Oncol. Feb. 20, 2014;32(6):579-86. doi: 10.1200/JCO.2012.45.2011. Epub Jan. 21, 2014.

Diaz et al. The molecular evolution of acquired resistance to targeted EGFR blockade in colotectal cancers. Natute. Jun. 28, 2012; 486(7404):537-40. doi: 10.1038/nature11219.

Diehl et al., Beaming: single-molcule PCR on microparticles in water-in-oil emulsions. Nat Methods. Jul. 2006;3(7):551-9.

Diehl et al., Circulating mutant DNA to assess tumor dynamics. Nat Med. Sep. 2008;14(9):985-90. doi:10.1038/nm.1789. Epub Jul. 31, 2007.

Diehl et al., Detection and quantification of mutations in the plasma of patients with colorectal tumors. Proc Natl Acad Sci U S A. Nov. 8, 2005;102(45):16368-73. Epub Oct. 28, 2005.

Dif-Couvreux et al., [Evaluation of conventional hemi nested PCR analysis for fetal RHD determination in maternal plasma]. J Gynecol Obstet Biol Reprod (Paris). Nov. 2006;35(7):658-64. French.

Dominguez et al., Wild-type blocking polymerase chain reaction for detection of single nucleotide minority mutations from clinical specimens. Oncogene. Oct. 13, 2005;24(45):6830-4. Erratum in: Oncogene. Jan. 26, 2006;25(4):656.

Dressman et al., Transforming single DNA molecules into fluorescent magnetic particles for detection and enumeration of genetic variations. Proc Natl Acad Sci U S A. Jul. 22, 2003;100(15):8817-22. Epub Jul. 11, 2003.

Eberhard et al., Mutations in the epidermal growth factor receptor and in KRAS are predictive and prognostic indicators in patients with non-small-cell lung cancer treated with chemotherapy alone and in combination with erlotinib. J Clin Oncol. Sep. 1, 2005;23(25):5900-9. Epub Jul. 25, 2005.

Ehrlich, DNA methylation in cancer: too much, but also too little. Oncogene. Aug. 12, 2002;21(35):5400-13.

Engelman et al., Allelic dilution obscures detection of a biologically significant resistance mutation in EGFR-amplified lung cancer. J Clin Invest. Oct. 2006;116(10):2695-706. Epub Aug. 10, 2006.

Fan et al., A versatile assay for high-throughput gene expression profiling on universal array matrices. Genome Res. May 2004;14(5):878-85.

Flaherty et al., Ultrasensitive detection of rare mutation using next-generation targeted resequencing. Nucleic Acid Res. Jan. 2012; 40(1):e2. doi: 10.1093/nar/gkr861. Epub Oct. 19, 2011.

Forshew et al., Noninvasive identification and monitoring of cance mutations by targeted deep sequencing of plasma DNA. Sci Transl Med. May 30, 2012; 4(136):136ra68. doi: 10.1126/scitranslmed.300726.

Frommer et al., A genomic sequencing protocol that yields a positive display of 5-methylcytosine residues in individual DNA strands. Proc Natl Acad Sci U S A. Mar. 1, 1992;89(5):1827-31.

Fuery et al., Detection of rare mutant alleles by restricition endonuclease-mediated selective-PCR: assay design and optimization. Clin Chem. May 2000;46(5):620-4.

Galbiati et al., Novel use of Full Cold-PCR protocol for noninvasive prenatal diagnosis of genetic diseases. Clin Chem. Jan. 2011;57(1):136-8. doi: 10.1373/clinchem.2010.155671. Epub Oct. 25, 2010.

Gao et al., DNA-guided genome editing using the Natronobacterium gregoryi Argonaute. Nat Biotechnol. Jul. 2016; 34(7):768-73. doi: 10.1038/nbt.3547. Epub May 2, 2016.

Gao et al., Retraction: DNA-guided genome editing using the Natronobacteroum gregoryi Argonaute. Nat Biotechnol. Aug. 8, 2017;35(8):797. doi: 10.1038/nbt0817-797a.

Genbank Accession No. L32764.1—Human coagulation factor v gene, exon 10 (GI: 488093, submitted Nov. 10, 1994, retrieved on Feb. 16, 2015 from http://www.ncbi.nlm.nih.gov/nuccore/L32764.1).

Giensendorf et al., Molecular beacons: a new approach for semiautomated mutation analysis. Clin Chem. Mar. 1998;44(3):482-6.

Girotti et al., Application of Sequencing, Liquid Biopsies, and Patient-Derived Xenografts for Personlized Medicine in Melanoma. Cancer Discov. Mar. 2016;6(3):286-99. doi: 10.1158/2159-8290.CD-15-1336. Epub Dec. 29, 2015.

Gnirke et al., Solution hybrid selection with ultra-long oligonucleotides for massively parallel targeted sequencing. Nat Biotechnol. Feb. 2009; 27(2):182-9. doi: 10.1038/nbt.1523. Epub Feb. 1, 2009.

Gonzalez et al., Microsatellite aleterations and TP53 mutations in plasma DNA of small-cell lung cancer patients: follow-up study and prognostic significance. Ann Oncol. Sep. 2000;11(9):1097-104.

Goodwin et al., Coming of age: ten years of next-generation sequencing technologies. Nat Rev Genet. May 17, 2016; 17(6):333-51. doi: 10.1038/nrg.2016.49.

Gray, Cancer: Genomics of metastasis. Nature. Apr. 15, 2010;464(7291):989-90. doi:10.1038/464989a.

Greenman et al., Patterns of somatic mutation in human cancer genomes. Nature. Mar. 8, 2007;446(7132):153-8.

Gregory et al., Targeted single molecule mutation detection with massively parallel sequencing. Nucleic Acids Res. Feb. 18, 2016; 44(3):e22. doi: 10.1093/nar/gkv915. Epub Sep. 17, 2015.

Grossi et al., Prognostic significance of K-ras, p53, bcl-2, PCNA, CD34 in radically resected non-small cell lung cancers. Eur J Cancer. Jun. 2003;39(9):1242-50.

Gu et al., Depletion of Abundant Sequences by Hybridization (DASH): using Cas9 to remove unwanted high-abundance species in sequencing libraries and molecular counting applications. Genome Biol. Mar. 4, 2016; 17:41. doi: 10.1186/s13059-016-0904-5.

Guatelli et al., Isothermal, in vitro amplification of nucleic acids by a multienzyme reaction modeled after retroviral replication. Proc Natl Acad Sci U S A. Mar. 1990;87(5):1874-8. Erratum in: Proc Natl Acad Sci U S A Oct. 1990;87(19):7797.

Guha et al., Differential strand separation at critical temperature: a minimally disruptive enrichment method for low-abundance unknown DNA mutations. Nucleic Acids Res. Feb. 1, 2013; 41(3):e50. doi: 10.1093/nar/gks1250. Epub Dec. 20, 2012.

Gundry et al., Amplicon melting analysis with labeled primers: a closed-tube method for differentiating homozygotes and heterozygotes. Clin Chem. Mar. 2003;49(3):396-406.

Gyllensten et al., Generation of single-stranded DNA by the polymerase chain reaction and its application to direct sequencing of the HLA-DQA locus. Proc Natl Acad Sci U S A. Oct. 1988;85(20):7652-6.

Heather et al., The sequence of sequencers: The history of sequencing DNA. Genomics. Jan. 2016; 107(1):1-8. doi: 10.1016/j.ygeno.2015.11.003. Epub Nov. 10, 2005.

Henikoff et al., Amino acid substitution matrices from protein blocks. Proc Natl Acad Sci U S A. Nov. 15, 1992;89(22):10915-9.

Hiatt et al., Single molecule molecular inversion probes for targeted, high-accuracy detection of low-frequency variation. Genome Res. May 2013; 23(5):843-54. doi: 10.1101/gr.147686.112. Epub Feb. 4, 2013.

Hibi et al., Molecular detection of genetic alterations in the serum of colotectal cancer patients. Cancer Res. Apr. 1, 1998;58(7):1405-7.

(56) References Cited

OTHER PUBLICATIONS

Higgins et al., Detection of tumor PIK3CA status in metastatic breast cancer using peripheral blood. Clin Cancer Res. Jun. 15, 2012; 18(12):3462-9. doi: 10.1158/1078-0432.CCR-11-2696. Epub Mar. 15, 2012.
Hindson et al., High-throuphput droplet digital PCR system for absolute quantitation of DNA copy number. Anal Chem. Nov. 15, 2011; 83(22):8604-10. doi: 10.10/ac20208g. Epub Oct. 28, 2011.
How-Kit et al., Ultrasensitive detection and identification of BRAF V600 mutations in fresh frozen, FFPE, and plasma samples of melanoma patients by E-ice-Cold-PCR. Anal Bioanal Chem. Sep. 2014; 406(22):5513-20. doi: 10.1007/s00216-014-7975-5. Epub Jun. 27, 2014.
Huang et al., Mutations in exon 7 and 8 of p53 as poor prognostic factors in patients with non-small cell lung cancer. Oncogene. May 14, 1998;16(19):2469-77.
Huang et al., Mutations of p53 and K-ras genes as prognostic factors for non-small cell lung cancer. Int J Oncol. Mar. 1998;12(3):553-63.
Igloi, Variablity in the stability of DNA-peptide nucleic acid (PNA) single-base mismatched duplexes: real-time hybridization during affinity electrophoresis in PNA-containing gels. Proc Natl Acad Sci U S A. Jul. 21, 1998;95(15):8562-7.
Ito et al., Tet proteins can convert 5-methylcytosine to 5-formylcytosine and 5-carboxylcytosine. Science. Sep. 2,2011; 333(6047):1300-3. doi: 10.1126/science.1210597. Epub Jul. 21, 2011.
Jackson et al., Specific p53 mutations detected in plasma and tumors of hepatocellular carcinoma patients by electrospray ionization mass spectrometry. Cancer Res. Jan. 1, 2001;61(1):33-5.
Janne et al., A rapid and sensitive enzymatic method for epidemal growth factor receptor mutation screening. Clin Cancer Res. Feb. 1, 2006;12(3 Pt 1):751-8.
Jee et al., Rates and mechanisms of bacterial mutagenesis from maximum-depth sequencing. Nature. Jun. 30, 2016; 534(7609):693-6. Epub Jun. 22, 2016.
Jeffreys et al., DNA enrichment by allele-specific hybridization (DEASH): a novel method for haplotyping and for detecting low-frequency base substitutional variants and recombinant DNA molecules. Genome Res. Oct. 2003;13(10):2316-24.
Johnson et al., Plasma nucleic acids in the diagnosis and management of malignant disease. Clin Chem. Aug. 2002; 48(8):1186-93.
Kanehisa, Use of statistical criteria for screening potential homologies in nucleic acid sequences. Nucleic Acids Res. Jan. 11, 1984;12(1 Pt 1):203-13.
Karlin et al., Applications and statistics for multiple high-scoring segments in molecular sequences. Proc Natl Acad Sci U S A. Jun. 15, 1993;90(12):5873-7.
Kheapko et al., Constant denaturant capillary electrophoresis (CDCE): a high resolution approach to mutational analysis. Nucleic Acids Res. Feb. 11, 1994;22(3):364-9.
Kimura et al., Mutant DNA in plasma of lung cancer patients: potential for monitoring response to therapy. Ann N Y Acad Sci. Jun. 2004;1022:55-60.
Kinde et al., Detection and quantification of rare mutations with massively parallel sequencing. Proc Natl Acad Sci U S A. Jun. 7, 2011; 108(23):9530-5. doi: 10.1073/pnas.1105422108. Epub May 17, 2011.
Koboldt et al., VarScan: variant detection in massively parallel sequencing of individual and pooled samples. Bioinformatics. Sep. 1, 2009; 25(17):2283-5. doi: 10.1093/bioinformatics/btp373. Epub Jun. 19, 2009.
Kopreski et al., Somatic mutation screening: identification of individuals harboring K-ras mutations with the use of plasma DNA. J Natl Cancer Inst. Jun. 7, 2000;92(11):918-23.
Kosaka et al., Mutations of the epidermal growth factor receptor gene in lung cancer: biological and clinicla implications. Cancer Res. Dec. 15, 2004;64(24):8919-23.
Koshkin et al., LNA (Locked Nucleic Acids): Synthesis of the adenine, cytosine, guanine, 5-methylcytosine, thymine and uracile bicyclonucleside monomers, oligomerisation, and unprecedented nucleic acid recognition. Tetrahedron. 1998;54(14):3607-30. doi:10.1016/s00404020(98)00094-5.
Kuang et al., Noninvasive detection of EGFR T790M in gefitinib or erlotinib resistant non-small cell lung cancer. Clin Cancer Res. Apr. 15, 2009; 15(8):2630-6. doi: 10.1158/1078-0432.CCR-08-2592. Epub Apr. 7, 2009.
Kulinski et al., Comparative calorimetric studies on the dynamic conformation of plant 5S rRNA: II. Structural interpretation of the thermal unfolding patterns for lupin seeds and wheat germ. Nucleic Acids Res. May 11, 1991;19(9):2449-55.
Kwoh et al., Transcription-based amplification system and detection of amplified human immunodeficiency virus type 1 with a bead-based sandwich hybridization format. Proc Natl Acad Sci U S A. Feb. 1989;86(4):1173-7.
Kwok, Finding a needle in a haystack: detection and quantification of rare mutant alleles are coming of age. Clin Chem. May 2000;46(5):593-4.
Kwok, High-throughput genotyping assay approaches. Pharmacogenomics. Feb. 2000;1(1):95-100.
Lander et al., Mapping mendelian factors underlying quantitative traits using RFLIP linkage maps. Genetics. Jan. 1982;121(1):185-99. Erratum in: Genetics Feb. 1994;136(2):705.
Latorra et al., Enhanced allele-specific PCR discrimination in SNP genotyping using 3' locked nucleic acid (LNA) primers. Hum Mutat,. Jul. 2003;22(1):79-85.
Lawrence et al., Mutational heterogeneity in cancer and the search for new cancer-associated genes. Nature. Jul. 11, 2013; 499(7457):214-218. doi: 10.1038/nature12213. Epub Jun. 16, 2013.
Lazaro et al., Mutation analysis of genetic diseases by asymmetric-PCR SSCP and ethidium bromide staining: application to neurofibromatosis and cystic fibrosis. Mol Cell Probes. Oct. 1992;6(5):357-9.
Li et al., Beaming up for detection and quantification of rare sequence variants. Nat Methods Feb. 2006;3(2):95-7.
Li et al., Coamplification at lower denaturation temperature-OCR increases mutation-detection selectivity of TaqMan-based real-time PCR. Clin Chem. Apr. 2009;55(4):748-56. doi:10.1373/clinchem.2008.113381. Epub Feb. 20, 2009.
Li et al., Cold-PCR: a new platform for highly improved mutation detection in cancer and genetic testing. Biochem Soc Trans. Apr. 2009;37(Pt 2):427-32. doi: 10.1042/BST0370427.
Li et al., Multiplex padlock targeted sequencing reveals human hypermutable CpG variations. Genome Res. Sep. 2009;19(9):1606-15. doi: 10.1101/gr.092213.109. Epub Jun. 12, 2009.
Li et al., Replacing PCR with Cold-PCR enriches variant DNA sequences and redefines the sensitivity of genetic testing. Nat Med. May 2008;14(5):579-84. doi: 10.1038/nm1708. Epub Apr. 13, 2008.
Li et al., s-RT-MELT for rapid mutation scanning using enzymatic selection and real time DNA-melting: new potential for multiplex genetics analysis. Nucleic Acids Res. 2007;35(12):e84. Epub Jun. 1, 2007.
Li et al., Two-round coamplification at lower denaturation temperature-PCR (Cold-PCR)-based sanger sequencing identifies a novel spectrum of low-level mutations in lung adenocarcinoma. Hum Mutat. Nov. 2009;30(11):1583-90. doi: 10.1002/humu.21112.
Liew et al., Genotyping of single-nucleotide polymorphisma by high-resolution melting of small amplicons. Clin Chem. Jul. 2004;50(7):1156-64.
Lipsky et al., DNA melting analysis for detection of single nucleotide polymorphisms. Clin Chem. Apr. 2001;47(4):635-44.
Li-Sucholeiki et al., A sensitive scanning for low frequency nuclear point mutations in human genomic DNA. Nucleic Acids Res. May 1, 2000;28(9):E44.
Liu et al., Denaturing high performance liquid chromatography (DHPLC) used in the detection of germline and somatic mutations. Nucleic Acids Res. Mar. 15, 1998;26(6):1396-400.
Liu et al., Detection of hotspot mutations and polymorphisms using an enhanced PCR-RFLP apprach. Hum Mutat. May 2003;21(5):535-41.
Liu et al., Inverse PCR-based RFLP scanning identifies low-level mutation signatures in colon cells and tumors. Cancer Res. Apr. 1, 2004;64(7):2544-51.

(56) References Cited

OTHER PUBLICATIONS

Llop et al., Development of a higly sensitive nested-PCR procedure using a single closed tube for detection of Erwinia amylovora in asymptomatic plant material. Appl Environ Microbiol. May 2000; 66(5):2071-8.

Lo et al., Plasma nucleic acid analysis by massively parallel sequencing: pathological insights and diagnostic implications. J Pathol. Nov. 2011; 225(3):318-23. doi: 10.1002/path.2960. Epub Aug. 24, 2011.

Lou et al., High-throughput DNA sequencing errors are reduced by orders of magnitude using circle sequencing. Proc Natl Acad Sci U S A. Dec. 2, 2013; 110(49):19872-7. doi: 10.1073/pnas.1319590110. Epub Nov. 15, 2013.

Luo et al., Detection of rare mutant K-ras DNA in a single-tube reaction using peptide nucleic acid as both PCR clamp and sensor probe. Nucleic Acids Res. Jan. 23, 2006;34(2):e12.

Luthra et al., Cold-PCR finds hot application in mutation analysis. Clin Chem. Dec. 2009;55(12):2077-8. doi: 10.1373/clinchem.2009.136143. Epub Oct. 15, 2009.

Makrigiorgos, PCR-based detection of minority point mutations. Hum Mutat. May 2004;23(5):406.12.

Mamon et al., Preferential amplification of apoptic DNA from plasma: potential for enhancing detection of minor DNA alterations in circulating DNA. Clin Chem. Sep. 2008;54(9):1582-4. doi:10.1373/clinchem.2008.104612.

Mancini et al., The use of Cold-PCR and high-reslouation melting analysis improves the limit of detection of KRAS and BRAF mutations in colorectal cancer. J Mol Diagn. Sep. 2010;12(5):705-11. doi: 10.235.3/jmoldx.2010.100018. Epub Jul. 8, 2010.

Mao et al., Synthesis of radioactive single-stranded DNA probes using aysmmetrical PCR and oligonucleotide random priming. Biotechniques. Oct. 1999;27(4):674-6, 678.

Margulies et al., Genome sequencing in microfabricated high-density picolitre reactors. Nature. Sep. 15, 2005;437(7057):376-80. Epub Jul. 31, 2005. Erratum in: Nature. May 4, 2006;441(7089):120. Ho, Chun He [corrected to Ho, Chun Heen].

Maulik et al., Novel non-isotopic detection of MutY enzyme-recognized mismatches in DNA via ultrasensitive detection of aldehydes. Nucleic Acids Res. Mar. 1, 1999;27(5):1316-22.

Mayall et al., Mutations of p53 gene can be detected in the plasma of patients with large bowel carcinoma. J Clin Pathol.Aug. 1998;51(8):611-3.

Mertes et al., Targeted enrichment of genomic DNA regions for next-generation sequencing. Brief Funct Genomics. Nov. 2011; 10(6):374-86. doi: 10.1093/bfgp/elr033. Epub Nov. 26, 2011.

Milbury et al., Cold-PCR enrichment of rare cancer mutation prior to targeted amplicon reequencing. Clin Chem. Mar. 2012; 58(3):580-9. doi: 10.1373/clinchem.2011.176198. Epub Dec. 21, 2011.

Milbury et al., Cold-PCR-enhanced high-resolution melting enables rapid and selective identification of low-level unknown mutations. Clin Chem. Dec. 2009;55(12):2130-43. doi: 10.1373/clinchem.2009.1310. Epub Oct. 8, 2009.

Milbury et al., Ice-Cold-PCR enables rapid amplification and robust enrichment for low-abundance unknown DNA mutations. Nucleic Acids Res. Jan. 2011;39(1):e2.doi: 10.1093/nar/gkq899. Epub Oct. 11, 2010.

Milbury et al., Multiplex amplification coupled with Cold-PCR and high resolution melting enables identification of low-abundance mutations in cancer samples with low DNA content. J Mol Diagn. Mar. 2011;(13)2:220-32. doi: 10.1016/j.jmoldx.2010.10.008.

Milbury et al., PCR-based methods for the enrichment of minority alleles and mutations. Clin Chem. Apr. 2009;55(4):632-40. doi:10.1373/clinchem.2008.113035. Epub Feb. 6, 2009.

Misale et al., Emergence of KRAS mutations and acquired resistance to anti-EGFR therapy in colorectal cancer. Nature. Jun. 28, 2012; 486(7404):532-6. doi: 10.1038/nature11156.

Mitra et al., Digital genotyping and haplotyping with polymerase colonies. Proc Natl Acad Sci U S A. May 13, 2003;100(10):5926-31. Epub May 2, 2003.

Mitra et al., Fluorescent in situ sequencing on polymerase colonies. Anal Biochem. Sep. 1, 2003;320(1):55-65. Erratum in: Anal Biochem. May 15, 2004;328(2):245.

Mitsudomi et al., Prognostic significance of p53 alterations in patients with non-small cell lung cancer: a meta-analysis. Clin Cancer Res. Oct. 2000;6(10):4055-63.

Montgomery et al., Simultaneous mutation scanning and genotyping by high-resolution DNA melting analysis. Nat Protoc. 2007;2(1):59-66.

Moorthie et al., Review of massively parallel DNA sequencing technologies. Hugo J. Dec. 2011; 5(1-4):1-12. doi: 10.1007/s11568-011-9156-3. Epub Oct. 27, 2011.

Murakami et al., p53 gene mutations are associated with shortened survival in patients with advanced non-small cell lung cancer: an analysis of medically managed patients. Clin Cancer Res. Feb. 2000;6(2):526-30.

Murphy et al., Enriching mutant sequences by modulating the denaturation time during PCR. Clin Chem. Jul. 2014;60(7):1014-6. doi: 10.1373/clinchem.2014.221465. Epub May 5, 2014.

Murphy et al., NRAS mutations with low allele burfen have independent prognostic significance for patients with lower risk myelodysplastic syndromes. Leukemia. Oct. 2013;27(10):2077-81. doi: 10.1038/leu.2013.160. Epub May 27, 2013.

Nagai et al., Development of a microchamber array for picoliter PCR. Anal Chem. Mar. 1, 2001;73(5):1043-7.

Nagai et al., High-throuput PCR in silicon based microchamber array. Biosens Bioelectron. Dec. 2001;16(9-12):1015-9.

Narayan et al., Ultrasensitive measurement of hotspot mutations in tumor DNA in blood using error-suppressed multiplexed deep sequencing. Cancer Res. Jul. 15, 2012; 72(14):3492-8. doi: 10.1158/0008-5472.CAN-11-4037. Epub May 10, 2012.

Newman et al., An ultrasensitive method for quantitating circulating tumor DNA with broad patient coverage. Nat Med. May 2014; 20(5):548-54. doi: 10.1038/nm.3519. Epub Apr. 6, 2014.

Newman et al., Integrated digital error suppression for improved detection of circulating tumor DNA. Nat Biotechnol. May 2016;34(5):547-555. doi: 10.1038/nbt.3520. Epub Mar. 28, 2016.

Nickerson et al., Random mutagenesis-PCR to introduce alterations into defined DNA sequences for validation of SNP and mutation detection methods. Hum Mutat. Mar. 2001;17(3):210-9.

Nilsen et al., The enzyme and the cDNA sequence of a thermolabile and double-strand specific DNase from Northern shrimps (Pandalus borealis). PLoS One. Apr. 22, 2010;5(4):e10295. doi: 10.1371/journal.pone.0010295.

Nollau et al., Methods for detection of point mutations: performance and quality assessment. IFCC Scientific Division, Committee on Molecular Biology Techniques. Clin Chem. Jul. 1997;43(7):1114-28.

Obika et al., Stability and structural features of the duplexes containing nucleoside analogues with a fixed N-type conformation, 2'-O,4'- C-methyleneribonucleosides. Tetrahedron Lett. 1998;39:5401-4.

Ogino et al., Sensitive sequencing method for KRAS mutation detection by Pyrosequencing. J Mol Diagn. Aug. 2005;7(3):413-21.

Oldenburg et al., Selective amplification of rare mutations using locked nucleic acid oligonucleotides that competitively inhibit primer binding to wild-type DNA. J Invest Dermatol. Feb. 2008;128(2):398-402. Epub Jun. 21, 2007.

Orita et al., Rapid and sensitive detection of point mutations and DNA polymorphisms using the polymerase chain reaction. Genomics. Nov. 1989;5(4):874-9.

Orum et al., Single base pair mutation analysis by PNA directed PCR clamping. Nucleic Acids Res. Nov. 25, 1993;21(23):5332-6.

Orum, PCR clamping. Curr Issues Mol Biol. Jan. 2000;2(1):27-30.

Oxnard et al., Noninvasive Detection of Response and Resistance in EGFR-Mutant Lung Cancer Using Quantitative Next-Generaton Genotyping of Cell-Free Plasma DNA. Clin Cancer Res. Mar. 15, 2014; 20(6):1698-1705. doi: 10.1158/1078-0432.CCR-13-2482. Epub Jan. 15, 2014.

Ozsolak, Third-generation sequencing techniques and applications to drug discovery. Expert Opin Drug Discov. Mar. 2012; 7(3):231-43. doi: 10.1517/17460441.2012.660145. Epub Feb. 2, 2012.

(56) References Cited

OTHER PUBLICATIONS

Paez et al., EGFR mutations in lung cancer: correlation with clinicial response to gefitinib therapy. Science. Jun. 4, 2004;304(5676):1497-500. Epub Apr. 29, 2004.

Paner et al., Analysis of melting transitions of the DNA hairpins formed from the oligomer sequences d[GGATAC(X)4GTATCC] (X = A, T, G, C). Biopolymers. Dec. 1990;29(14):1715-34.

Pearson et al., Improved tools for biological sequence comparison. Proc Natl Acad Sci U S A. Apr. 1988;85(8):2444-8.

Persson et al., Four-color multiplex reverse transcription polymerase chain reaction—overcoming its limitations. Anal Biochem. Sep. 1, 2005;344(1):33-42.

Petrie et al., Deep sequencing analysis of mutations resulting from the incorporation of dNTP analogs. Nucleic Acids Res. Dec. 2010;38(22):8095-104. doi:10.1093/nar/gkq685. Epub Aug. 6, 2010.

Pinzani et al., BRAFV600E detection in melanoma is highly improved by Cold-PCR. Clin Chim Acta. May 12, 2011;412(11-12):901-5. doi: 10.1016/j.cca.2011.01.014. Epub Jan. 22, 2011.

Pomp et al., Organic solvents as facilitators of polymerase chain reaction. Biotechniques. Jan. 1991;10(1):58-9.

Porreca et al., Polony DNA sequencing. Curr Protoc Mol Biol. Nov. 2006;Chapter 7:Unit 7.8. doi: 10.1002/0471142727.mb0708s76.

Qin et al., Ultra deep sequencing detects a low rate of mosaic mutations un sclerosis complex. Hum Genet. Mar. 2010;127(5):573-82. doi: 10.1007/s00439-010-0801-z. Epub Feb. 18, 2010.

Qiu et al., Duplex-specific nuclease-mediated bioanalysis. Trends Biotechnol. Mar. 2015;33(3):180-8. doi: 10.1016/j.tibtech.2014.12.008. Epub Jan. 29, 2015.

Raja et al., Temperature-controlled primer limit for multiplexing of rapid, quantitative reverse transcription-PCR assays: application to intraoperative cancer diagnostics. Clin Chem. Aug. 2002;48(8):1329-37.

Reckamp et al., A Highly Sensitive and Quantitative Test Platform for Detection of NSCLC EGFR Mutations in Urine and Plasma. J Thorac Oncol. Oct. 2016; 11(10):1690-700. doi: 10.1016/j.jtho.2016.05.035. Epub Jul. 25, 2016.

Reed et al., Sensitivity and specificity of single-nucleotide polymorphism scanning by high-resolution melting analysis. Clin Chem. Oct. 2004;50(10):1748-54. Epub Aug. 12, 2004.

Rehbein et al., Comparison of different methods to produce single-strand DNA for identification of canned tuna by single-strand conformation polymorphism analysis. Electrophoresis. Jun. 1998;19(8-9):1381-4.

Reis-Filho, Next-generation sequencing. Brease Cancer Res. 2009;11 Suppl 3:S12. doi: 10.1186/bcr2431. Epub Dec. 18, 2009.

Richardson et al., Beaming up personalized medicine: mutation detection in blood. Clin Cancer Res. Jun. 15, 2012; 18(12):3209-11. doi: 10.1158/1078-0432.CCR-12-0871. Epub May 1, 2012.

Riesewijk et al., Monoallelic expression of human PEG1/MEST is paralleled by parent-specific methylation in fetuses. Genomics. Jun. 1, 1997;42(2):236-44.

Roschewski et al., Circulating tumour DNA and CT monitoring in patients with untreated diffuse large B-cell lymphoma: a correlative biomarker study. Lancet Oncol. May 2015;16(5):541-9. doi: 10.1016/S1470-2045(15)70106-3. Epub Apr. 1, 2015.

Saiki et al., Enzymatic amplification of beta-globin genomic sequences and restriction site analysis for diagnosis of sickle cell anemia. Science. Dec. 20, 1985;230(4732):1350-4.

Sanchez et al., Two-temperature Late-PCR endpoint genotyping. BMC Biotechnol. Dec. 4, 2006;6:44.

Saunders et al., Interlaboratory study on thermal cycler performance in controlled PCR and random amplified polymorphic DNA analyses. Clin Chem. Jan. 2001;47(1):47-55.

Schmitt et al., Detection of ultra-rare mutations by next-generation sequencing. Proc Natl Acad Sci U S A. Sep. 4, 2012; 109(36):14508-13. doi: 10.1073/pnas.1208715109. Epub Aug. 1, 2012.

Schuermann et al., PNA clamping techniques for the determination of oncogene mutations. Methods Mol Biol. 2002;208:165-79.

Schuermann, Detection of K-ras and p53 mutations by "mutant-enriched" PCR-RFLP. Methods Mol Med. 2003;75:325-33.

Schwaederle et al., Use of Liquid Biopsies in Clinical Oncology: Pilot Experience in 168 Patients. Clin Cancer Res. Nov. 15, 2016; 22(22):5497-5505. doi: 10.1158/1078-0432.CCR-16-0318. Epub May 16, 2016.

Seyama et al., A novel blocker-PCR method for detection of rare mutant alleles in the presence of an excess amount of normal DNA. Nucleic Acids Res. May 25, 1992;20(10):2493-6.

Shagin et al., A novel method for SNP detection using a new duplex-specific nuclease from crab hepatopancreas. Genome Res. Dec. 2002; 12(12):1935-42.

Shah et al., Mutational evolution in a lobular breast tumour profiled at single nucleotide resolution. Nature. Oct. 8, 2009;461(7265):809-13. doi: 10.1038/nature08489.

Shao et al., p53 mutation in plasma DNA and its prognostic value in breast cancer patients. Clin Cancer Res. Aug. 2001;7(8):2222-7. Retraction in: Shao ZM, Wu J, Shen ZZ, Nguyen M. Clin Cancer Res. Sep. 2002;8(9):3027.

Shi et al., Ultra-sensitive detection of BRAF V600E and G469A mutations by Ice Cold-PCR and Blocker sequencing. Sep. 2011 Poster.

Shi et al., Use of Blocker Sequencing (Blocking Oligonucleotide Cycle Sequencing) after Ice Cold-PCR for detection of K-RAS and BRAF mutations. May 2011, Poster.

Shigematsu et al., Clinical and biological features associated with epidermal growth factor receptor gene mutations in lung cancers. J Natl Cancer Inst. Mar. 2, 2005;97(5):339-46.

Silva et al., Tumor DNA in plasma at diagnosis of breast cancer patients is a valuable predictor of disease-free survival. Clin Cancer Res. Dec. 2002;8(12):3761-6.

Siravegna et al., Clonal evolution and resistance to EGFR blockade in the blood of colorectal cancer patients. Nat Med. Jul. 2015; 21(7):795-801. doi: 10.1038/nm.3870. Epub Jun. 1, 2015.

Smith et al., Comparison of biosequences. Adv Appl Math. Dec. 1981;2(4):482-9. doi:10.1016/01968858(81)90046-4.

Song et al., DMSO Increases Mutation Scanning Detection Sensitivity of High-Resolution Melting in Clinical Samples. Clin Chem. Nov. 2015; 61(11):1354-62. doi: 10.1373/clinchem.2015.245357. Epub Oct. 2, 2015.

Song et al., Elimination of unaltered DNA in mixed clinical samples via nuclease-assisted minor-allele enrichment. Nucleic Acids Res. Nov. 2, 2016; 44(19):e146, Epub Jul. 18, 2016.

Ståhlberg et al., Simple, multiplexed, PCR-based barcoding of DNA enable sensitive mutation detection in liquid biopsies using sequencing. Nucleic Acids Res. Jun. 20, 2016;44(11):e105. doi: 10.1093/nar/gkw224. Epub Apr. 7, 2016.

Steger, Thermal denaturation of double-stranded nucleic acids: prediction of temperatures critical for gradient gel electrophoresis and polymerase chain reaction. Nucleic Acids Res. Jul. 25, 1994;22(14):2760-8.

Sun et al., Detection of tumor mutations in the presence of excess amounts of normal DNA. Nat Biotechnol. Feb. 2002;20(2):186-9.

Suspène et al., Inversing the natural hydrogen bonding rule to selectively amplify GC-rich ADAR-edited RNAs. Nucleic Acids Res. Jul. 2008;36(12):e72. doi: 10.1093/nar/gkn295. Epub May 30, 2008.

Tang et al., Characterization of mitochondrial DNA heteroplasmy using a parallel sequencing system. Biotechniques. Apr. 2010;48(4):287-96. doi:10.2144/000113389.

Taniguchi et al., Quantitative detection of EGFR mutations in circulating tumor DNA derived from lung adenocarcinomas. Clin Cancer Res. Dec. 15, 2011; 17(24):7808-15. doi: 10.115/1078-0432.CCR-11-1712. Epub Oct. 5, 2011.

Thierry et al., Clinical validation of the detection of KRAS and BRAF mutations from circulating tumor DNA. Nat Med. Apr. 2014; 20(4):430-5,. doi: 10.1038/nm.3511. Epub Mar. 23, 2014.

Thomas et al., High-throughput oncogene mutation profiling in human cancer. Nat Genet. Mar. 2007;39(3):347-51. Epub Feb. 11, 2007. Erratum in: Nat Genet. Apr. 2007;39(4):567. Macconnaill, Laura E [corrected to MacConaill, Laura].

Thomas et al., Sensitive mutation detection in heterogeneous cancer specimens by massively parallel picoliter reactor sequencing. Nat Med. Jul. 2006;12(7):852-5. Epub Jun. 25, 2006. Erratum in: Nat Med. Oct. 2006;12(10):1220.

(56) References Cited

OTHER PUBLICATIONS

Thress et al., Acquired EGFR C797S mutation mediates resistance to AZD9291 in non-small cell lung cancer harboring EGFR T790M. Nat Med. Jun. 2015; 21(6):560-2. doi: 10.1038/nm.3854. Epub May 4, 2015.

Till et al., High-throughput discovery of rare human nucleotide polymorphisms by Ecotilling. Nucleic Acids Res. Aug. 7, 2006;34(13):e99. Erratum in: Nucleic Acids Res. 2006;34(18):5352.

Tong et al., Diagnostic developments involving cell-free (circulating) nucleic acids. Clin Chim Acta. Jan. 2006;363(1-2):187-96. Epub Aug. 26, 2005.

Tsang et al., Circulating nucleic acids in plasma/serum. Pathology. Apr. 2007;39(2):197-207.

Vámosi et al., The helix-coil transition of DNA duplexes and hairpins observed by multiple fluorescence parameters. Biochemistry. Oct. 6, 1998;37(40):14300-16.

Varley et al., Bisulfite Patch PCR enables multiplexed sequencing of promoter methylation across cancer samples. Genomes Res. Sep. 2010; 20(9):1279-87. doi: 10.1101/gr.101212.109. Epub Jul. 13, 2010.

Varley et al., Nested Patch PCR enables highly multiplexed mutation discovery in candidate genes. Genome Res. Nov. 2008; 18(11):1844-50. doi: 10.1101/gr.078204.108. Epub Oct. 10, 2008.

Varley et al., Nested Patch PCR for highly multiplexed amplification of genomic loci. Cold Spring Harb Protoc. Jul. 2009; 2009(7):pdb.prot5252. doi: 10.1101/pdb.prot5252.

Vestheim et al., Blocking primers to enhance PCR amplification of rare sequences in mixed samples—a case study on prey DNA in Antarctic krill stomachs. Front Zool. Jul. 20, 2008;5:12. doi: 10.1186/1742-9994-5-12.

Volker et al., High-resolution calorimetric and optical melting profiles of DNA plasmids: resolving contributions from intrinsic melting domains and specifically designed inserts. Biopolymers. Sep. 1999;50(3):303-18. Erratum in: Biopolymers Jan. 2000;53(1):112.

Wagner et al., Challenges for biomarkers in cancer detection. Ann N Y Acad Sci. Jun. 2004;1022:9-16.

Walker et al., Strand displacement amplification—an isothermal, in vitro DNA amplification technique. Nucleic Acids Res. Apr. 11, 1992;20(7): 1691-6.

Walsh et al., Preferential PCT amplification of alleles: mechanisms and solutions. PCR Methods Appl. May 1992;1(4):241-50.

Wang et al., Determination of human beta(2)-adrenoceptor haplotypes by denaturation selective amplification and subtractive genotyping. Am J Pharmacogenomics. 2001;1(4):315-22.

Wetmur, DNA probes: applications of the principles of nucleic acid hyrbridization. Crit Rev Biochem Mol Biol. 1991;26(3-4):227-59.

Wittwer et al., High-resolution genotyping by amplicon melting analysis using LCGreen. Clin Chem. Jun. 2003;49(6 Pt 1):853-60.

Wittwer et al., The LightCycler: a microvolume multisample fluorimeter with rapid temperature control. Biotechniques. Jan. 1997;22(1):176-81.

Wong et al., Multiplex Illumina sequencing using DNA barcoding. Curr Protoc Mol Biol. 2013;Chapter 7:Unit 7.11.. doi: 10.1002/0471142727.mb0711s101.

Worm et al., In-tube DNA methylation profiling by fluorescence melting curve analysis. Clin Chem. 2001;47(7):1183-9.

Wu et al., Continuosly tunable nucleic acid hybridization probes. Nat. Methods. Dec. 2015;12(12):1191-6. doi: 10.1038/nmeth.3626. Epub Oct. 19, 2015.

Xu et al., Dual primer emulsion PCR for next-generation DNA sequencing. Biotechniques. May 2010;48(5):409-12. doi: 10.2144/000113423.

Yeung et al., Enzymatic mutation detectiong technologies. Biotechniques. May 2005;(38)(5):749-58.

Yu et al., Base-resolution analysis of 5-hydroxymethylcytosine in the mammalian genome. Cell. Jun. 8, 2012; 149(6):1368-80. doi: 10.1016/j.cell.2012.04.027. Epub May 17, 2012.

Zhang et al., An amplification and ligation-based method to scan for unknown mutations in DNA. Hum Mutat. Aug. 2002;20(2):139-47.

Zhao et al., p53 gene mutations in non-small cell lung cancer detected by polymerase chain reaction single-strand conformation polymoorpism analysis. Chin Med Sci J. Sep. 1999;14(3):134-7.

Zhou et al., Closed-tube genotyping with unlabled oligonucleotide probes and a saturating DNA dye. Clin Chem. Aug. 2004;50(8):1328-35. Epub May 27, 2004.

Zuo et al., Application of Cold-PCR for improved detection of KRAS mutation in clinical samples. Mod Pathol. Aug. 2009;22(8):1023-31. doi:10.1038/modpathol.2009.59. Epub May 8, 2009.

\* cited by examiner

Singletube- MT-WT mixing- duplex single-tube ICE-COLD
Including RS for both KRAS and BRAF Cycling: INCLUDES ICE COLD PCR CYCLING FOR LAST 15 CYCLES

| Step | Temperature (°C) | Time |
|---|---|---|
| Initial denat | 98 | 120 sec |
| 10 cycles | 98 | 10 sec |
| | Ta=65 (outer) | 60 sec |
| | 72 | 30 sec |
| 4 cycles | 98 | 10 sec |
| | Ta=68 (anchors) | 30 sec |
| | 72 | 15 sec |
| 20 cycles | 98 | 10 sec |
| | Ta=63 (Tails) | 30 sec |
| | 72 | 15 sec |
| 15 cycles | 98 | 10 sec |
| | 78 | 30 sec |
| | 80.5 | 30 sec |
| | Ta=63 (Tails) | 30 sec |
| | 72 | 10 sec |
| Final ext | 72 | 300 sec |
| Melt Curve | | |

RA 06/09/2017

SAMPLES IN DUPLICATE

| Sample ID | Ct | Melt Peak |
|---|---|---|
| MT in WT ratio 1:5 | 14.76 | 85.14 |
| MT in WT ratio 1:5 | 14.97 | 85.15 |
| MT in WT ratio 1:10 | 32.73 | 84.61 |
| MT in WT ratio 1:10 | 33.25 | 84.69 |
| MT in WT ratio 1:30 | 33.37 | 84.83 |
| MT in WT ratio 1:30 | 33.26 | 84.96 |
| MT in WT ratio 1:100 | 33.09 | 85.25 |
| MT in WT ratio 1:100 | 33.38 | 85.24 |
| HMC alone | 33.8 | 85.05 |
| NTC | 0 | 85.34 |

FIG. 4

METHODS AND COMPOSITIONS FOR SELECTING AND AMPLIFYING DNA TARGETS IN A SINGLE REACTION MIXTURE

RELATED APPLICATIONS

This Application is a national stage filing under 35 U.S.C. 371 of International Patent Application Serial No. PCT/US2018/043506, filed Jul. 24, 2018, which claims the benefit under 35 USC 119(e) of U.S. provisional patent application Ser. No. 62/536,187, filed Jul. 24, 2017, the entire contents of each of which are incorporated by reference herein.

BACKGROUND OF THE INVENTION

Next generation sequencing (NGS) is currently widely employed in the field of personalized medicine to derive the molecular profile of human specimens such as those obtained from cancer biopsies, blood, urine or other excretions. Molecular profiling of patient specimens can have broad diagnostic, prognostic or predictive information for the course of diseases like cancer. Preparation of patient specimens for NGS and targeted re-sequencing usually involves several steps that can last several days, thus increasing the time to obtaining results which can be important to the patients and their treatments. Longer sample preparation times also unavoidably result in higher costs.

SUMMARY OF THE INVENTION

This disclosure relates to compositions and methods for single-step, multi-stage amplification reactions that combine many stages of sample preparation process in a single tube reaction. The disclosed technology provides a mean of performing multiplexed nested PCR in a single vessel, without any need of purification steps. In some embodiments, the rapid and streamlined sample preparation methods result in highly specific coverage of the targeted DNA sites, thus improving the efficiency of NGS and reducing costs. Such multi-stage PCR reactions may optionally include enrichment steps like COLD-PCR or NaME-PrO. The disclosed compositions and methods are also particularly suited for sensitive and effective sequencing of low-level or less abundant mutations via the incorporation of molecular barcodes.

The present disclosure is based on the discovery that serial amplification reactions can be carried out in a single vessel when one understands and takes advantage of the subtle relationship between temperature conditions, concentration of oligonucleotides, and annealing and melting temperature (typically determined by length) of oligonucleotides. The disclosed technology is based on the use of three sets of primers: a pair of outer primers, a pair of inner primers that are nested within the pair of outer primers, and tail primers that are complementary to tails on the inner primers. By adjusting the temperature conditions, annealing temperatures of the primers, number of amplification cycles, and the concentrations of the outer, inner, and tail primers, it is possible to carry out multiplexed nested PCR in a single vessel. See for example, FIG. 1. In summary, one can selectively drive amplification through any one of the three sets of primers, as desired.

One way to implement the ability to selectively amplify is based primarily on varying the concentration and annealing temperatures of the primers. In one such embodiment, the concentration of the outer primers is lower than, or in the range of primer concentrations that are typically used in PCR (e.g., 0.01-0.2 µM). The concentration of the inner primers is relatively much lower than the concentration of the outer primers, such that carrying out amplification cycles at the annealing temperature of the outer primers favors outer primer binding due to the greater concentration of the outer primers. The inner primer concentration is lower than the outer primer concentration, such that if the outer primers were absent, or if the first step of amplification of any one of the methods described herein were not performed, then amplification using the inner primers would yield only a relatively insignificant amount of product from the DNA sample (e.g., about 100 times less, 1000 times less, 10,000 times less, or 100,000 times less). When amplifying at temperatures favorable to inner primer binding but above a temperature favorable to outer primer binding, one achieves amplification driven by inner primer binding. The inner primers, which are nested within the outer primers, provide another level of specificity to any one of the disclosed methods herein. Finally, the bulk of the amplification can occur by using tail primers with annealing temperatures above those for the outer and inner primers, driving amplification solely through the tail primers.

Provided in the single reaction vessel are (i) a sample of double-stranded DNA (e.g., genomic DNA, or cDNA); (ii) a set of outer multiplexed primers; (iii) a set of inner multiplexed primers; and (iv) a set of tail primers. The kinetic conditions of the reaction can be altered to favor the annealing of the set of outer multiplexed primers over the set of inner multiplexed primers. For example, if both sets of primers are the same length and present at the same concentration, and have the same melting temperature (Tm) and annealing temperature (Ta), the primers will anneal similarly. However, if the set of outer multiplexed primers are present in an excess (e.g., 10× excess) compared to the inner multiplexed primers, they will anneal more favorably than the set of inner multiplexed primers. If the set of outer multiplexed primers are longer than the set of inner multiplexed primers and their annealing temperature is above the temperature that allows the set of inner multiplexed primers to anneal, this will favor annealing of the set of outer multiplexed primers at temperatures above the annealing temperature of the inner multiplexed primers. Once the PCR product generated by the outer multiplexed primers starts building up, the increased concentration of the amplified region will now offer ample template for the inner primers to also bind substantially and generate PCR product which is nested to the product produced by the outer primers, and thereby being highly specific to the intended DNA targets. Finally, the set of tail primers will anneal after the set of outer multiplexed primers and after the set of inner multiplexed primers because the tail sequence is not present in the template DNA until after the amplification reaction with the inner multiplexed primers. The tail primers can be selected, for example, to be short with a relatively low annealing temperature but at a relatively high concentration, such that conditions can be applied to favor binding of the tail primer.

In another embodiment, the outer multiplex primers are at a concentration that is lower than the inner multiplex primers and the outer multiplex primers have an annealing temperature that is higher than that of the inner multiplex primers. If temperatures are applied at the annealing temperature of the outer multiplex primers (above the annealing temperature of the inner multiplex primers), then the outer multiplex primers will anneal and extend. Following repeated such extensions, then the temperature can be brought to the annealing temperature of the inner multiplex primers (which is lower than the annealing temperature of the outer multiplex primers) and these conditions will favor the annealing of the inner multiplex primers because the inner multiplex primers are at a higher concentration than the outer multiplex primers. Following repeated such extensions, then the tail primers may be annealed and extended. If the tail primers are at a higher concentration and have a lower annealing temperature than the inner and outer multiplex primers, then the temperature can be brought to the tail primer annealing temperature, and these conditions will favor the annealing of the tail primers because the tail primers are at a higher concentration than the inner and outer multiplex primers.

It therefore can be understood that the outer multiplexed primers, the inner multiplexed primers and the tail primers can be in the same vessel, and the various reactions (first outer primer extension, then inner primer extension, and then tail primer extension) can be carried out in the desired order in that single vessel, based on selecting appropriate primers, concentrations (e.g., primer concentrations) and temperature conditions. This provides extraordinary advantages over the procedures of the prior art.

In one aspect, provided are methods for selecting and amplifying DNA targets in a single reaction vessel. The methods comprise the following steps:
(a) providing in the single reaction vessel:
   a sample of double-stranded DNA (e.g., genomic DNA, or cDNA),
   a set of outer multiplexed primers comprising an outer forward primer and an outer reverse primer, wherein each of the outer forward and reverse primers complement target nucleic acids on the DNA,
   a set of inner multiplexed primers comprising an inner forward primer and an inner reverse primer, wherein each of the inner forward and reverse primers comprises a target-specific anchor on its 3' end, and the inner forward primer comprises a common forward tail on its 5' end and the inner reverse primer comprises a common reverse tail on its 5' end, wherein the common forward tail is different from the common reverse tail,
   a set of tail primers comprising of a first tail primer and a second tail primer, wherein the first tail primer is complementary to the common forward tail and the second tail primer is complementary to the common reverse tail;
(b) subjecting the provided contents in the single reaction vessel to an amplification condition which favors the annealing of the set of outer multiplexed primers to the DNA;
(c) subjecting the provided contents in the single reaction vessel to an amplification condition which favors annealing of the set of inner multiplexed primers to amplified products of step (b); and
(d) subjecting the provided contents in the single reaction vessel to an amplification condition under which the set of tail primers anneal to the amplified products of step (c).

In another aspect, provided are methods of selecting and amplifying DNA targets in a single reaction vessel. The methods comprise the following steps:
(a) providing in the single reaction vessel:
   a sample of fragmented double-stranded DNA (e.g., genomic DNA, or cDNA) comprising a unique identifier and a common tag at the 5' end and at the 3' end,
   a set of outer multiplexed primers comprising an outer forward primer and an outer reverse primer, (i) wherein the outer forward primer complements the common tag and the outer reverse primer complements target nucleic acids on the DNA, or (ii) the outer reverse primer complements the common tag and the outer forward primer complements target nucleic acids on the DNA,
   a set of inner multiplexed primers comprising an inner forward primer and an inner reverse primer, wherein (ii) the inner forward primer is complementary to the common tag, which comprises a common forward tail, and wherein the inner reverse primer comprises a target-specific anchor on its 3' end and a common reverse tail on its 5' end, or (ii) the inner reverse primer is complementary to the common tag, which comprises a common reverse tail, and wherein the inner forward primer comprises a target-specific anchor on its 3' end and a common forward tail on its 5' end,
   wherein the common forward tail is different from the common reverse tail,
   a set of tail primers comprising of a first tail primer and a second tail primer, wherein the first tail primer is complementary to the common forward tail and the second tail primer is complementary to the common reverse tail;
(b) subjecting the provided contents in the single reaction vessel to an amplification condition which favors the annealing of the set of outer multiplexed primers to the DNA;
(c) subjecting the provided contents in the single reaction vessel to an amplification condition which favors annealing of the set of inner multiplexed primers to amplified products of step (b); and
(d) subjecting the provided contents in the single reaction vessel to an amplification condition under which the set of tail primers anneal to the amplified products of step (c).

As used herein, "selection of DNA targets or target sequences" means picking out target DNA sequences to amplify. A DNA target may be selected on the basis of a known region of mutation, or to search for an unknown mutation in a DNA sample. For example, a particular DNA sequence may be targeted for determine the presence of a particular mutation that may cause, or aid in the diagnosis of a particular disease. In some embodiments, a DNA target is selected as a control. By virtue of selecting a sequence of particular consecutive base pairs in a DNA and performing any one of the methods disclosed herein, one is selectively amplifying that sequence.

In some embodiments, the methods further comprise providing in the single reaction vessel a DNA polymerase, dNTPs and an amplification buffer.

In some embodiments, annealing temperatures of the inner multiplexed primers is 3-20° C. (e.g., 3-5, 3-10, 5-10, 5-15, 5-20, or 10-20° C.) different from annealing temperature of the outer multiplexed primers. In some embodiments, annealing temperatures of the inner multiplexed primers is 3-20° C. (e.g., 3-5, 3-10, 5-10, 5-15, 5-20, or 10-20° C.) lower than the annealing temperature of the outer multiplexed primers. In some embodiments, the annealing temperature of the outer multiplexed primers is 60-65° C., and the annealing temperature of the inner multiplexed primers is 50-55° C. In some embodiments, the annealing temperatures of the inner multiplexed primers is 3-20° C. (e.g., 3-5, 3-10, 5-10, 5-15, 5-20, or 10-20° C.) higher than the annealing temperature of the outer multiplexed primers. In some embodiments, the annealing temperature of the outer multiplexed primers is 58-62° C., and the annealing temperature of the inner multiplexed primers is 66-70° C. In some embodiments, the annealing temperature of the tail primers is 3-20° C. (e.g., 3-5, 3-10, 5-10, 5-15, 5-20, or 10-20° C.) different from the annealing temperature of the inner multiplexed primers. In some embodiments, the annealing temperature of the tail primers is 60-70° C.

In some embodiments, the inner multiplexed primers are hot start primers, activated by subjecting the provided contents in the single reaction vessel to an activation temperature after the completion of step (b). In some embodiments, the tail primers are hot start primers, activated by subjecting the provided contents in the single reaction vessel to an activation temperature after the completion of step (c). In some embodiments, the activation temperature is 90-95° C. In certain embodiments, the provided contents in the single reaction vessel is subjected to an activation temperature for 5 seconds to 5 minutes.

In some embodiments, the concentration of outer multiplexed primers is 0.01-0.2 µM. In certain embodiments, the concentration of inner multiplexed primers is 0.001-0.04 µM. In some embodiments, the concentration of tail primers is 0.1-1 µM. In some embodiments, the ratio of concentration of outer multiplexed primers to the concentration of inner multiplexed primers is 0.25-2000. In certain embodiments, the ratio of the concentration of the tail primers to the concentration of inner multiplexed primers is 5:200. In some embodiments, the ratio of the concentration of the tail primer to the concentration of the outer multiplexed primers is 1-20.

In some embodiments, the amplification of step (b) is carried out for 8-12 cycles. In certain embodiments, the amplification of step (c) is carried out for 2-6 cycles. In some embodiments, the amplification of step (d) is carried out for 10-30 cycles. In certain embodiments, the number of amplification cycles in step (b) exceeds the number of amplification cycles in step (c). In some embodiments, the number of amplification cycles in step (d) exceeds the number of amplification cycles in step (c). In certain embodiments, the number of amplification cycles in step (d) exceeds the number of amplification cycles in step (b).

In some embodiments, the tail primers further comprise 20-30 bp of a 3'end portion of a sequencing adapter. In certain embodiments, the inner forward and inner reverse primers each further comprise, between the target-specific anchor and the common forward or reverse tails, a central portion that is a unique barcode. In some embodiments, the unique barcode is 8-14 bp in length. In some embodiments, the inner multiplexed primers are provided such that the ratio of DNA (e.g., genomic DNA, or cDNA) to unique barcodes is $10^7$-$10^9$ unique barcodes to 100 ng DNA.

In some embodiments, the methods further comprise enriching mutant alleles of the target nucleic acids relative to wild-type alleles of the target nucleic acids after the completion of step (d). In some embodiments, the enriching the mutant alleles of the target regions relative to wild-type alleles of the target nucleic acids comprises subjecting the provided contents in the single reaction vessel after the completion of step (d) to one or more of the following: Nuclease-assisted Minor-allele Enrichment using Probe Overlap (NaME-PrO), Coamplification at Lower Denaturation temperature-PCR (COLD-PCR), Improved and Complete Enrichment COLD-PCR (ice-COLD-PCR), Temperature-Tolerant-ice-COLD-PCR (TT-ice-COLD-PCR), toehold PCR and Differential Strand Separation at Critical Temperature (DiSSECT). In some embodiments, step (d) comprises one or more of the following: Coamplification at Lower Denaturation temperature-PCR (COLD-PCR), Improved and Complete Enrichment COLD-PCR (ice-COLD-PCR), Temperature-Tolerant-ice-COLD-PCR (TT-ice-COLD-PCR), and toehold PCR.

In some embodiments, step (d) comprises subjecting the provided contents in the single reaction vessel to one or more of the following: Coamplification at Lower Denaturation temperature-PCR (COLD-PCR), Improved and Complete Enrichment COLD-PCR (ice-COLD-PCR), and Temperature-Tolerant-ice-COLD-PCR (TT-ice-COLD-PCR). In some embodiments, COLD-PCR, ice-COLD-PCR, TT-ice-COLD-PCR, or toehold PCR comprise the last amplification cycles of step (d). In some embodiments, at least the first four (e.g., 4, 5, 6, 7, 8, 9, 10, or more) amplification cycles of step (d) do not comprise COLD-PCR, ice-COLD-PCR, TT-ice-COLD-PCR, or toehold PCR. For example, step (d) may comprise four amplification cycles of normal PCR followed by 10 cycles of COLD-PCR using tail primers.

In some embodiments, the enrichment of mutant alleles of the target nucleic acids relative to wild-type alleles of the target nucleic acids by Coamplification at Lower Denaturation temperature-PCR (COLD-PCR), Improved and Complete Enrichment COLD-PCR (ice-COLD-PCR), or Temperature-Tolerant-ice-COLD-PCR (TT-ice-COLD-PCR) is performed in the same tube in which steps (a), (b), (c) and (d) were performed. This is only possible for COLD-PCR, ice-COLD-PCR, TT-ice-COLD-PCR, or toehold PCR. For NAME-PRO and DISSECT it has to be separate steps than step (d). In further embodiments, the reagents for the enrichment of mutant alleles of the target nucleic acids relative to wild-type alleles of the target nucleic acids are provided in step (a).

In some embodiments, DNA is obtained from a biological sample. In some embodiments, the biological sample is selected from the group consisting of: tissue, blood, plasma, serum, urine, saliva and cerebrospinal fluid. In some embodiments, the biological sample is fixed or frozen. In certain embodiments, the biological sample is formalin-fixed paraffin-embedded (FFPE).

In another aspect, provided are reaction mixtures. The reaction mixtures comprise:

a set of outer multiplexed primers that complement target nucleic acids on DNA (e.g., genomic DNA, or cDNA), a set of outer multiplexed primers comprising an outer forward primer and an outer reverse primer, wherein each of the outer forward and reverse primers complement target nucleic acids on the DNA, a set of inner multiplexed primers comprising an inner forward primer and an inner reverse primer, wherein each of the inner forward and reverse primers comprises a target-specific anchor on its 3' end, and the inner forward primer comprises a common forward tail on its 5' end and the inner reverse primer comprises a common reverse tail on its 5' end, wherein the common forward tail is different from the common reverse tail, a set of tail primers comprising of a first tail primer and a second tail primer, wherein the first tail primer is complementary to the common forward tail and the second tail primer is complementary to the common reverse tail.

In another aspect, provided are reaction mixtures. The reaction mixtures comprise:

a set of outer multiplexed primers comprising an outer forward primer and an outer reverse primer, (i) wherein the outer forward primer complements a common tag and the outer reverse primer complements target nucleic acids on DNA (e.g., genomic DNA, or cDNA), or (ii) the outer reverse primer complements a common tag and the outer forward primer complements target nucleic acids on DNA, a set of inner multiplexed primers comprising an inner forward primer and an inner reverse primer, wherein (ii) the inner forward primer is complementary to the common tag, which comprises a common forward tail, and wherein the inner reverse primer comprises a target-specific anchor on its 3' end and a common reverse tail on its 5' end, or (ii) the inner reverse primer is complementary to the common tag, which comprises a common reverse tail, and wherein the inner forward primer comprises a target-specific anchor on its 3' end and a common forward tail on its 5' end, wherein the common forward tail is different from the common reverse tail, and a set of tail primers comprising of a first tail primer and a second tail primer, wherein the first tail primer is complementary to the common forward tail and the second tail primer is complementary to the common reverse tail.

In some embodiments, the outer forward primer, the inner forward primer, and the first tail primer are common for all target nucleic acids. In some embodiments, the outer reverse primer, the inner reverse primer, and the second tail primer are common for all target nucleic acids. In further embodiments, the primers that are common for all targets are hot start primers.

Sequences of any double-stranded DNA can be amplified in the methods disclosed herein. In some embodiments, double-stranded DNA is genomic DNA. In some embodiments, double-stranded DNA is cDNA. Genomic DNA can be sourced or obtained from a biological sample (e.g., circulating DNA, a sample of tissue (e.g., a fixed or frozen sample of tissue), urine, blood, plasma, serum, saliva, or cerebrospinal fluid). In some embodiments, the reaction mixtures further comprise a sample of DNA (e.g., genomic DNA, or cDNA). In some embodiments, the DNA is sourced from a biological sample sourced from tissue, blood, plasma, serum, urine, saliva or cerebrospinal fluid. In some embodiments, the biological sample is fixed or frozen.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 4 depicts PCR cycling conditions applied for single-tube, all-in-one reaction for two targets BRAF and KRAS amplified directly from genomic DNA in one reaction, including also mutation enrichment for both targets.

DETAILED DESCRIPTION

Figure 1:
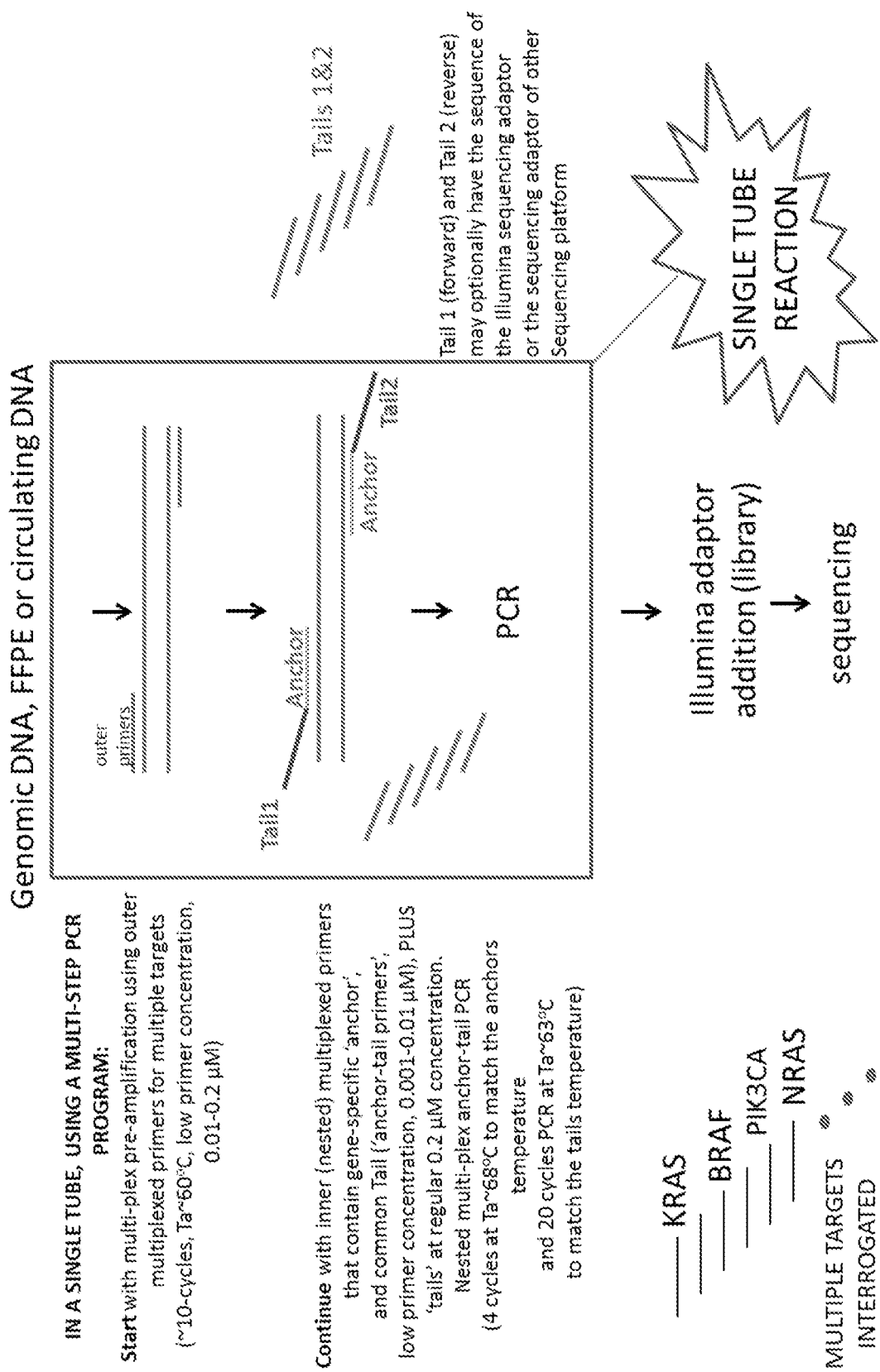
FIG. 1 describes a single tube, all-in-one reaction to select DNA targets of interest and add the sequencing adaptors in a single multi-stage PCR. Majority of the final PCR product is generated by the Tail oligonucleotides, which are at higher concentration than other oligonucleotides in the reaction.

The present disclosure, in one aspect, relates to compositions and methods for highly efficient and specific sample preparation in a single tube to provide sequencing-ready DNA that combines (a) DNA target selection; (b) optional incorporation of molecular barcodes for quantification of mutation abundance, and (c) optional mutation enrichment for increasing sequencing efficiency and reducing costs. This is achieved by using multi-stage PCR reactions as described in subsequent sections.

The present disclosure is based on the discovery that serial amplification reactions can be carried out in a single vessel when one understands the subtle relationship between temperature, concentration, length of oligonucleotides, and number of amplification cycles. Provided in the single reaction vessel are (i) a sample of double-stranded DNA (e.g., genomic DNA, or cDNA); (ii) a set of outer multiplexed primers; (iii) a set of inner multiplexed primers; and (iv) a set of tail primers. The kinetic conditions of the reaction can be altered to favor the annealing of the set of outer multiplexed primers over the set of inner multiplexed primers (and over the tail primers). For example, if both sets of primers are the same length and present at the same concentration, and have the same melting temperature (Tm) and annealing temperature (Ta), the primers will anneal similarly. However, if the set of outer multiplexed primers are present in a 10× excess, they will anneal more favorably than the set of inner multiplexed primers. If the set of outer multiplexed primers are longer than the set of inner multiplexed primers and their annealing temperature is above the temperature that allows the set of inner multiplexed primers to anneal, this will favor annealing of the set of outer multiplexed primers. Once the PCR product generated by the outer multiplexed primers starts building up, the increased concentration of the amplified region will now offer ample template for the inner primers to also bind substantially and generate PCR product which is nested to the product produced by the outer primers, and thereby being highly specific to the intended DNA targets. Finally, the set of tail primers will anneal after the set of outer multiplexed primers and after the set of inner multiplexed primers because the tail sequence is not present in the template DNA until after the amplification reaction with the inner multiplexed primers.

If the difference in one of the following factors: annealing temperature (which is dependent partly on the length) of primers, concentration of primers, and amplification cycles between different steps of any one of the methods disclosed herein, is high, then the difference in the other factors may be lower. For example, if the difference in the annealing temperatures for the outer and inner primers is high (e.g., greater than 10° C.), then the difference in the concentrations of the outer primers and inner primers may be less (e.g., less than 200 times, or less than 20 times). Similarly, if the difference in the annealing temperatures for the tail and inner primers is high (e.g., greater than 5, 10, 15 or 20° C.), then the difference in the concentrations of the tail primers and inner primers may be less (e.g., less than 500 times, less than 200 times, less than 20 times, or less than 2 times). On the other hand, if the difference in the annealing temperatures for the outer and inner primers is low (e.g., 10° C. or less), then a higher ratio of concentrations of the outer and inner primers may be utilized (e.g., 200 times or more, or 20 times or more). Or, if the if the difference in the annealing temperatures for the tail and inner primers is low (e.g., less than 20, 15, 10, 5, or 3° C.), then a higher difference in the concentrations of the tail primers and inner primers may be utilized (e.g., 20, 200, 100, or 10,000 times or more).

As is shown in FIG. 1, the methods disclosed herein provide for selecting and amplifying DNA targets in a single reaction vessel by subjecting the provided contents in the single reaction vessel to an amplification condition which favors the annealing of the set of outer multiplexed primers to the DNA (e.g., step (b)); an amplification condition which favors annealing of the set of inner multiplexed primers to amplified products of step (b) (e.g., step (c)); and an amplification condition under which the set of tail primers anneal to the amplified products of step (c). In some embodiments, the provided contents in the reaction vessel are subjected to an amplification condition which favors annealing of the set of outer multiplexed primers first, an amplification condition which favors annealing of the set of inner multiplexed primers second, and an amplification condition under which the set of tail primers anneal third.

For example, in the first step of FIG. 1 (e.g., step (a)), the contents of the reaction, including the three sets of primers and the genomic DNA, are provided to the reaction vessel. In the second step of FIG. 1 (e.g., step (b)), the set of outer multiplexed primers, which are complementary to the genomic DNA, anneal to the genomic DNA and amplify a segment of the genomic DNA. In the third step of FIG. 1 (e.g., step (c)), the set of inner multiplexed primers anneal to the amplified genomic DNA. The inner multiplexed primers have a portion that is complementary to the genomic DNA and is nested relative to the outer multiplexed primers, and have a tail portion. A shorter segment of genomic DNA is amplified having tail segments attached to the ends. In the fourth step of FIG. 1 (e.g., step (d)), the tail primers anneal to the tail segments on the amplification product from step (c) and the genomic DNA portion having tail segments at the end is further amplified. Each of these steps will be discussed in further detail below.

In some embodiments, the sample of DNA (e.g., genomic DNA, or cDNA) is obtained from a biological sample. The term "biological sample" refers to any sample including tissue samples (such as tissue sections and needle biopsies of a tissue) and cell samples (e.g., cytological smears (such as Pap or blood smears) or samples of cells obtained by microdissection). Other examples of biological samples include blood, plasma, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. In some embodiments, the biological sample is fixed or frozen. In some embodiments, the biological sample is formalin-fixed paraffin-embedded (FFPE).

As is used herein, a "reaction vessel" may be any suitable container for subjecting the DNA (e.g., genomic DNA, or cDNA) and primers of the claims to the amplification conditions of the claims. In some embodiments, the reaction vessel is suitable for subjecting DNA and primers to polymerase chain reaction (PCR). In some embodiments, the reaction vessel comprises a tube (e.g., a test tube, a PCR tube, or a capillary tube). In some embodiments, the reaction vessel comprises a well of a plate (e.g., a PCR plate).

As used herein, "primers' refers to oligonucleotides that anneal to opposite strands of a target sequence so as to form an amplification product during a PCR reaction.

Outer Multiplex Primers

The methods described herein for selecting and amplifying DNA targets in a single reaction vessel, in some embodiments, comprise subjecting the provided contents in the single reaction vessel to an amplification condition which favors the annealing of the set of outer multiplexed primers to the DNA (e.g., genomic DNA, or cDNA) as shown in the second step of FIG. 1 (e.g., step (b)). In some embodiments, the provided contents in the reaction vessel are subjected to the amplification condition which favors annealing of the set of outer multiplexed primers before the amplification condition which favors annealing of the set of inner multiplexed primers or an amplification condition under which the set of tail primers anneal. In some embodiments, in the single-reaction tube assay described herein, this amplification condition will favor the annealing of the set of outer multiplexed primers to the DNA because (i) the annealing temperature of the outer multiplex primers is higher than the annealing temperature of the inner multiplex primers, hence keeping the primer annealing temperature high prevents the inner primers from binding at this higher temperature, and (ii)

because template DNA comprising the tail sequence has not yet been generated (i.e., the tail primers do not have template DNA to bind to). In addition, the outer multiplex primers can be present at a higher concentration than the inner multiplex primers, further favoring the annealing of the outer multiplex primers at temperatures above the annealing temperature of the inner multiplex primers. In some embodiments, in the single-reaction tube assay described herein, this amplification condition will favor the annealing of the set of outer multiplexed primers to the DNA because (i) the outer multiplex primers are present at a higher concentration than the inner multiplex primers, (ii) the annealing temperature of the outer multiplex primers is lower than the annealing temperature of the inner multiplex primers, but the higher concentration of the outer primers favors outer primer annealing at or below the outer primer annealing temperature, and (iii) because template DNA comprising the tail sequence has not yet been generated (i.e., the tail primers do not have template DNA to bind to).

In some embodiments, the annealing temperature ($T_a$) of the set of outer multiplex primers is about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. In some embodiments, the $T_a$ of the set of outer multiplex primers is about 55° C. to about 70° C. In some embodiments, the $T_a$ of the set of outer multiplex primers is about 60° C. to about 65° C. In some embodiments, the $T_a$ of the set of outer multiplex primers is about 58° C. to about 62° C.

In some embodiments, the contents in the single reaction vessel are subjected to amplification at the annealing temperature of outer multiplex primers for 6, 7, 8, 9, 10, 11, 12, 13, or 14 cycles. In some embodiments, the contents in the single reaction vessel are subjected to amplification at the annealing temperature of the set of outer multiplex primers for more than 14 cycles. In some embodiments, the contents in the single reaction vessel are subjected to amplification at the annealing temperature of the set of outer multiplex primers for 6-14 cycles, or 8-12 cycles.

In some embodiments, the outer multiplex primers comprise an outer forward primer and an outer reverse primer. In some embodiments, the outer forward and reverse primers complement target nucleic acids on the DNA (e.g., genomic DNA, or cDNA).

In some embodiments, either the outer forward primer or the outer reverse primer complements a common tag and the other primer complements target nucleic acids on the DNA (e.g., genomic DNA, or cDNA).

In some embodiments, the outer forward primer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the outer forward primer is greater than 40 nucleotides in length. In some embodiments, the outer forward primer is about 10 to 40 nucleotides, or about 15-35 nucleotides in length.

In some embodiments, the outer reverse primer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the outer reverse primer is greater than 40 nucleotides in length. In some embodiments, the outer reverse primer is about 10 to 40 nucleotides, or about 15-35 nucleotides in length.

The concentration of the outer primers (forward and reverse outer primers) is selected to be lower than, or in the range of primer concentrations that are typically used in PCR. It is selected so that the outer primers make very little product compared to the inner and tail primers. This is to avoid amplification of mis-primed targets, especially in samples of genomic DNA, where the likelihood of mis-priming is particularly high.

In some embodiments, the concentration of the outer forward primer is 0.005 to 0.4 µM. In some embodiments, the concentration of the outer forward primer is 0.01 to 0.2 µM. In some embodiments, the concentration of the outer forward primer is 0.005, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.30, or 0.40 µm.

In some embodiments, the concentration of the outer reverse primer is 0.005 to 0.4 µM. In some embodiments, the concentration of the outer reverse primer is 0.01 to 0.2 µM. In some embodiments, the concentration of the outer reverse primer is 0.005, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.30, or 0.40 µm.

In some embodiments, provided in the single reaction vessel are two or more sets of outer multiplexed primers that are complementary to two or more different targets. In some embodiment, the at least two sets of outer multiplexed primers is at least 5, 10, 15, 20, 30, 40, 50, 100, 200, 500, 1,000, 5,000, 10,000 or 30,000 outer multiplexed primers.

Inner Multiplex Primers

The methods described herein for selecting and amplifying DNA targets in a single reaction vessel, in some embodiments, comprise subjecting the provided contents in the single reaction vessel to a second amplification condition which favors the annealing of the set of inner multiplexed primers to amplified products of the outer multiplexed primers as shown in the third step of FIG. 1 (e.g., step (c)). In some embodiments, the provided contents in the reaction vessel are subjected to the second amplification condition which favors annealing of the set of inner multiplexed primers after the amplification condition which favors annealing of the set of outer multiplexed primers and before an amplification condition under which the set of tail primers anneal. In some embodiments, in the single-reaction tube assay described herein, the inner multiplex primers are at a concentration that is lower than the concentration of the outer multiplex primers but the annealing temperature of the inner multiplex primers is above the annealing temperature of the outer multiplex primers. The second amplification condition will favor the annealing of the set of inner multiplexed primers to the product amplified by the outer multiplex primers, for example, if the annealing is carried out at a temperature above the annealing temperature of the outer multiplex primers (and above the annealing temperature of the tail primers). In embodiments of the single-reaction tube assay described herein, the second amplification condition will favor the annealing of the set of inner multiplexed primers versus the outer multiplex primers and the tail primers. Amplification by the set of tail primers can predominantly occur third, in part, because the tail primers amplify only the amplification product of the inner multiplexed primers.

In some embodiments, the annealing temperature ($T_a$) of the set of inner multiplex primers is about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. In some embodiments, the $T_a$ of the set of inner multiplex primers is about 45° C. to about 60° C., or about 50° C. to about 55° C. In some embodiments, the $T_a$ of the set of inner multiplex primers is about 66° C. to about 70° C.

In some embodiments, the annealing temperatures of the inner multiplexed primers is different from annealing temperature of the outer multiplexed primers. In some embodiments, the annealing temperatures of the inner multiplexed primers is 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. different from annealing temperature of the outer multiplexed primers. In some embodiments, the annealing temperatures of the inner multiplexed primers is 1° C.-50° C. different from annealing temperature of the outer multiplexed primers. In some embodiments, the annealing temperatures of the inner multiplexed primers is 3° C. -20° C. different from annealing temperature of the outer multiplexed primers.

In some embodiments, the annealing temperatures of the inner multiplexed primers is lower than the annealing temperature of the outer multiplexed primers. In some embodiments, the annealing temperatures of the inner multiplexed primers is 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. lower than the annealing temperature of the outer multiplexed primers. In some embodiments, the annealing temperatures of the inner multiplexed primers is 1° C.-50° C. lower than the annealing temperature of the outer multiplexed primers. In some embodiments, the annealing temperatures of the inner multiplexed primers is 3° C. -20° C. lower than the annealing temperature of the outer multiplexed primers. In some embodiments, the annealing temperature of the outer multiplexed primers is 60-65° C., and the annealing temperature of the inner multiplexed primers is 50-55° C.

In some embodiments, the annealing temperatures of the inner multiplexed primers is higher than the annealing temperature of the outer multiplexed primers. In some embodiments, the annealing temperatures of the inner multiplexed primers is 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. higher than the annealing temperature of the outer multiplexed primers. In some embodiments, the annealing temperatures of the inner multiplexed primers is 1° C.-50° C. higher than the annealing temperature of the outer multiplexed primers. In some embodiments, the annealing temperatures of the inner multiplexed primers is 3° C.-20° C. higher than the annealing temperature of the outer multiplexed primers. In some embodiments, the annealing temperature of the outer multiplexed primers is 58-62° C., and the annealing temperature of the inner multiplexed primers is 66-70° C.

In some embodiments, the contents in the single reaction vessel are subjected to amplification at the annealing temperature of the set of inner multiplex primers for 1, 2, 3, 4, 5, 6, 7, 8, 9, or 10 cycles. In some embodiments, the contents in the single reaction vessel are subjected to amplification at the annealing temperature of the set of inner multiplex primers for 2-8 cycles, or 2-6 cycles.

In some embodiments, the number of amplification cycles in the amplification condition which favors the annealing of the set of outer multiplexed primers to the DNA (e.g., step (b)) exceeds the number of amplification cycles in the amplification condition which favors the annealing of the set of inner multiplexed primers to amplified products of the outer multiplexed primers (e.g., step (c)). In some embodiments, step (b) exceeds step (c) by 2, 3, 4, 5, 6, 7, 8, 9, 10, 11, 12, 13, 14, or 15 cycles.

In some embodiments, the inner multiplex primers comprise an inner forward primer and an inner reverse primer. In some embodiments, each of the inner forward and reverse primers comprises a target-specific anchor on its 3' end (e.g., an forward and reverse target-specific anchor), and the inner forward primer comprises a common forward tail on its 5' end and the inner reverse primer comprises a common reverse tail on its 5' end. In some embodiments, the target-specific anchor of the inner forward primer is 3' to the outer forward primer. In some embodiments, the target-specific anchor of the inner reverse primer is 5' to the outer reverse primer.

In some embodiments, (ii) the inner forward primer is complementary to the common tag, which comprises a common forward tail, and wherein the inner reverse primer comprises a target-specific anchor on its 3' end and a common reverse tail on its 5' end, or (ii) the inner reverse primer is complementary to the common tag, which comprises a common reverse tail, and wherein the inner forward primer comprises a target-specific anchor on its 3' end and a common forward tail on its 5' end.

In some embodiments, the common forward tail is different from the common reverse tail.

In some embodiments, the forward target-specific anchor is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the forward target-specific anchor is greater than 40 nucleotides in length. In some embodiments, the forward target-specific anchor is about 10 to 40 nucleotides, or about 15-35 nucleotides in length.

In some embodiments, the reverse target-specific anchor is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the reverse target-specific anchor is greater than 40 nucleotides in length. In some embodiments, the reverse target-specific anchor is about 10 to 40 nucleotides, or about 15-35 nucleotides in length.

In some embodiments, the common forward tail comprises sequence that is common to all of the inner forward primers. In some embodiments, the common reverse tail comprises sequence that is common to all of the inner reverse primers. In some embodiments the common forward tail and the common reverse tail comprise sequencing primer sequence. In some embodiments, the tail primers comprise 15, 16, 17, 18, 19, 20, 21, 22, 23, 24, 25, 26, 27, 28, 29, 30, 31, 32, 33, 34, or 35 base pairs, e.g., 20-30 base pairs of a 3'end portion of a sequencing adapter. In some embodiments the common forward tail and the common reverse tail comprise NGS adaptor sequence. In some embodiments, the common forward tail and the common reverse tail comprise Illumina® sequencing adaptor sequence. In some embodiments, the common forward tail and the common reverse tail comprise Qiagen® sequencing adaptor sequence. In some embodiments, the common forward tail and the common reverse tail comprise Ion Torrent® sequencing adaptor sequence.

In some embodiments, the common forward tail is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the common forward tail is greater than 40 nucleotides in length. In some embodiments, the common forward tail is about 10 to 40 nucleotides, or about 15-35 nucleotides, or about 20-30 nucleotides in length.

In some embodiments, the common reverse tail is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the common reverse tail is greater than 40 nucleotides in length. In some embodiments, the common reverse tail is about 10 to 40 nucleotides, or about 15-35 nucleotides, or about 20-30 nucleotides in length.

In some embodiments, the concentration of the inner primers (forward and reverse inner primers) is selected to be much lower than the concentration of outer primers, such that if the outer primers were absent, or if the first step of amplification of any one of the methods described herein were not performed, then amplification using the inner primers would yield only an insignificant amount of product from the DNA sample (e.g., about 100 times less, 1000 times less, 10,000 times less, or 100,000 times less). In some embodiments, the concentration of the inner forward primer is 0.0005 to 0.08 µM. In some embodiments, the concentration of the inner forward primer is 0.001 to 0.04 µM. In some embodiments, the concentration of the inner forward primer is 0.0005, 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.030, 0.040, 0.050, 0.060, 0.070, or 0.080 µM.

In some embodiments, the concentration of the inner reverse primer is 0.0005 to 0.08 µM. In some embodiments, the concentration of the inner reverse primer is 0.001 to 0.04 µM. In some embodiments, the concentration of the inner reverse primer is 0.0005, 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.030, 0.040, 0.050, 0.060, 0.070, or 0.080 µM.

Figure 3:
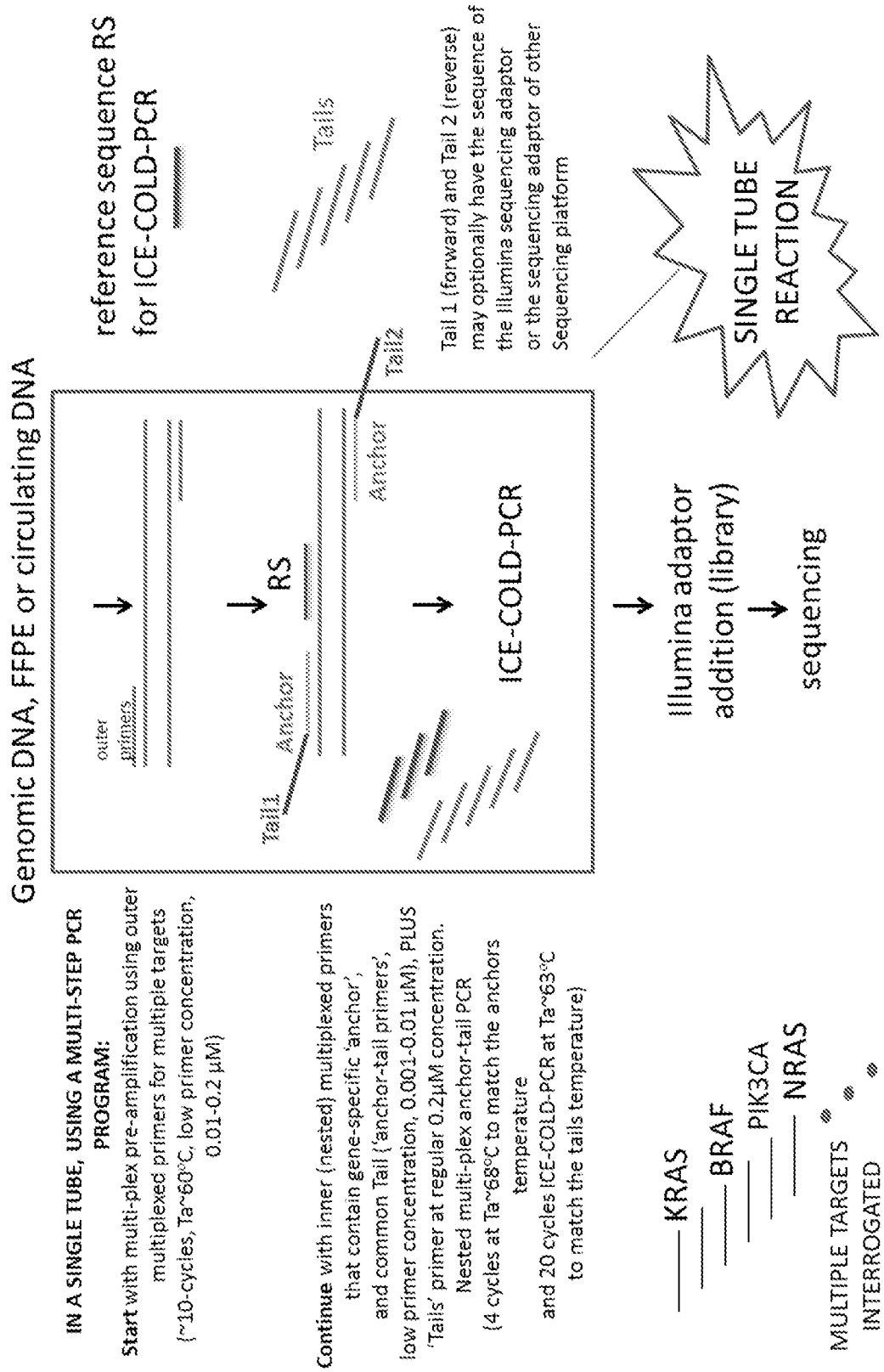
FIG. 3 describes single step 'all in one' reaction incorporating target selection as well as mutation enrichment via COLD-PCR/ICE-COLD-PCR.
Figure 7:
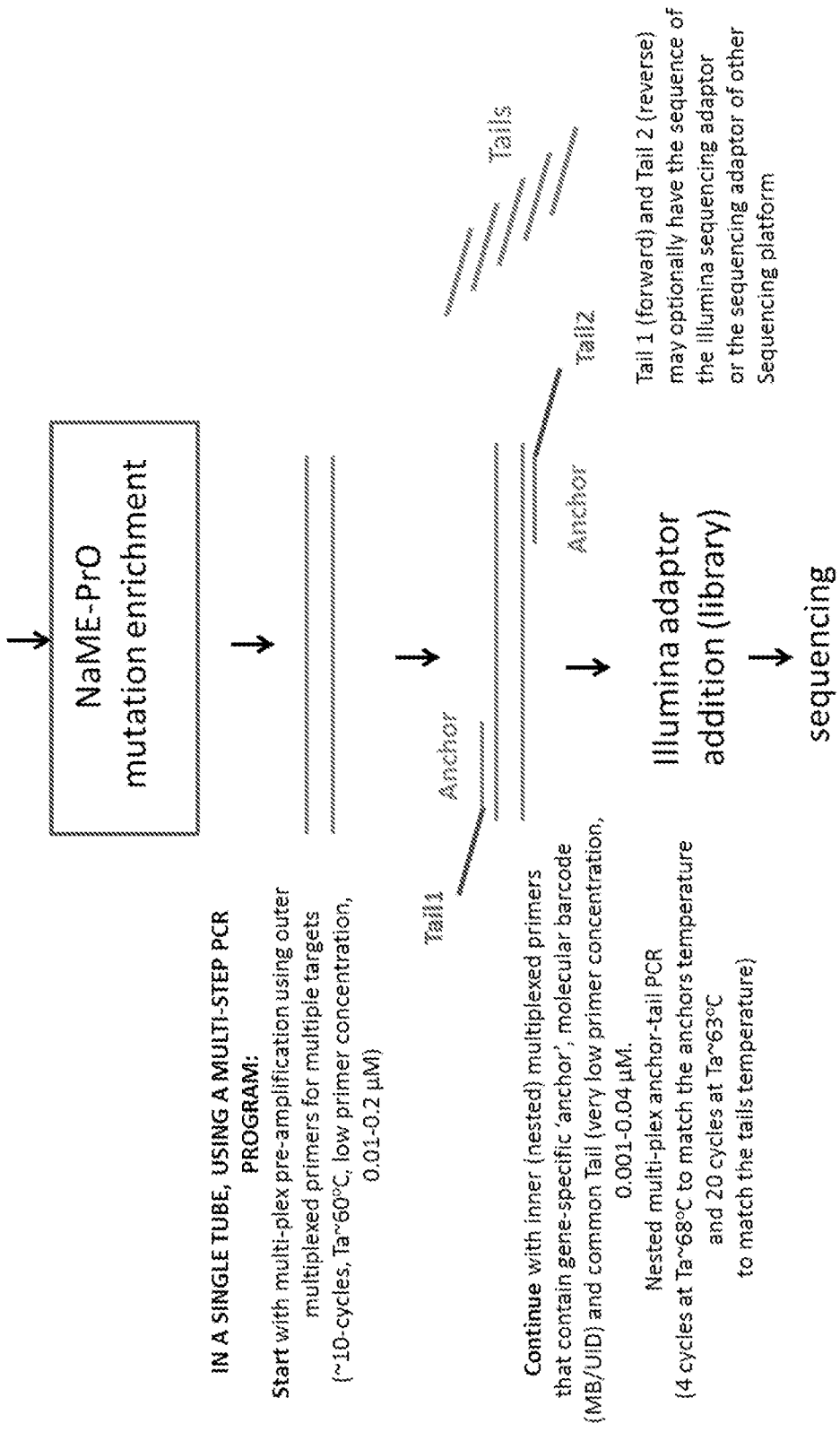
FIG. 7 describes multiplexed mutation enrichment directly on genomic DNA via NaME-PrO (as described in Nucleic Acid Research November 2016, Song et al), followed by single-tube, all-in-one target selection, to yield sequencing-ready DNA highly enriched in mutations.

As detailed in the Summary section above and as is made clear in FIG. 1, 3, or 7, in some embodiments, the ratio of concentration of the inner multiplexed primers to the concentration of outer multiplexed primers is 2:10, 2:20, 2:30, 2:40, 2:50, 2:60, 2:70, 2:80, 2:90, 2:100, 2:120, 2:140, 2:160, 2:180, 2:200, 2:220, 2:240, 2:260, 2:280, 2:300, 2:320, 2:340, 2:360, 2:380, 2:400, 2:450, 2:500, 2:550, 2:600, 2700, 2:800, 2:900, 2:1000, 2:1100, 2:1200, 2:1300, 2:1400, 2:1500, 2:1600, 2:1700, 2:1800, 2:1900, or 2:2000. In some embodiments, the ratio of concentration of the outer multiplexed primers to the concentration of inner multiplexed primers is 2:20-2:2000. In some embodiments, the ratio of concentration of the outer multiplexed primers to the concentration of inner multiplexed primers is 2:100-2:300.

In some embodiments, the concentration of outer primers compared to the concentration of inner primers is significantly high so that if the outer primers were absent, the inner primers would not make a significant amount of product from the DNA sample as a template. In some embodiments, the ratio of the concentration of the outer multiplexed primers to the concentration of inner multiplexed primers is 0.25-2000 (e.g., 0.25-2000, 0.25-200, 0.25-50, 0.25-20, 0.25-2, 2-2000, 1-2000, 1-200, 1-50, 1-20, 1-2, 2-2000, 2-200, or 2-20). For example, the concentration of outer multiplexed primers may be 0.01-0.2 µM (e.g., 0.01-0.2, or 0.02-0.1 µM) and the concentration of inner multiplexed primers may be 0.0001-0.04 µM (e.g., 0.0001-0.04, or 0.001-0.01 µM)

In some embodiments, provided in the single reaction vessel are two or more sets of inner multiplexed primers that are complementary to two or more different targets. In some embodiment, the at least two sets of outer multiplexed primers is at least 5, 10, 15, 20, 30, 40, 50, 100, 200, 500, 1,000, 5,000, 10,000 or 30,000 outer multiplexed primers.

Tail Primers

The methods described herein for selecting and amplifying DNA targets in a single reaction vessel, in some embodiments, comprise subjecting the provided contents in the single reaction vessel to an amplification condition under which the set of tail primers anneal to the amplified products of the inner multiplexed primers as shown in the fourth step of FIG. 1 (e.g., step (d)). In some embodiments, the provided contents in the reaction vessel are subjected to the amplification condition under which the set of tail primers anneal after the amplification condition which favors annealing of the set of outer multiplexed primers and after the amplification condition which favors annealing of the set of inner multiplexed primers. In some embodiments, in the single-reaction tube assay described herein, the tail primers will anneal in this amplification condition because (i) the outer multiplexed primers will predominantly amplify first because the outer multiplex primers are present at a higher concentration than the inner multiplex primers, (ii) the inner multiplexed primers will then predominantly amplify second, and (iii) amplification by the set of tail primers will predominantly occur third, because the tail primers amplify the amplification product of the inner multiplexed primers. In some embodiments, the tail primers anneal only at a temperature below the annealing temperature of the outer and inner multiplex primers. In these embodiments, the tail primers are typically at a higher concentration than the outer and inner multiplex primers, such that tail primer annealing will be favored when the temperature is at or below the annealing temperature of the tail primer.

In some embodiments, the annealing temperature ($T_a$) of the set of tail primers is about 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C. In some embodiments, the $T_a$ of the set of tail primers is about 55° C. to about 70° C., or about 60° C. to about 70° C.

In some embodiments, the annealing temperatures of the tail primers is different from annealing temperature of the inner multiplexed primers. In some embodiments, the annealing temperatures of the tail primers is 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C. or 50° C. different from annealing temperature of the inner multiplexed primers. In some embodiments, the annealing temperatures of the tail primers is 1° C.-50° C. different from annealing temperature of the inner multiplexed primers. In some embodiments, the annealing temperatures of the tail primers is 3° C.-20° C. different from annealing temperature of the inner multiplexed primers.

In some embodiments, the contents in the single reaction vessel are subjected to amplification at the annealing temperature of the set of tail primers for 11, 12, 13, 14, 15, 16, 17, 18, 19, 20, 21, 22, 23, 24, 25, 26, 27, 28, 29, or 30 cycles.

In some embodiments, the contents in the single reaction vessel are subjected to amplification at the annealing temperature of the set of tail primers for more than 30 cycles. In some embodiments, the contents in the single reaction vessel are subjected to amplification at the annealing temperature of the set of tail primers for 10-30 cycles.

In some embodiments, the number of amplification cycles in an amplification condition under which the set of tail primers anneal to the amplified products of the inner multiplexed primers (e.g., step (d)) exceeds the number of amplification cycles in the amplification condition which favors the annealing of the set of inner multiplexed primers to amplified products of the outer multiplexed primers (e.g., step (c)). In some embodiments, step (d) exceeds step (c) by 5, 6, 7, 8, 9, 10, 11, 12, 13, 14, 15, 16, 17, 18, 19, 20, 21, 22, 23, 24, 25, 26, 27, 28, 29, or 30 or more cycles.

In some embodiments, the number of amplification cycles in an amplification condition under which the set of tail primers anneal to the amplified products of the inner multiplexed primers (e.g., step (d)) exceeds the number of amplification cycles in the amplification condition which favors the annealing of the set of outer multiplexed primers to the DNA (e.g., step (b)). In some embodiments, step (d) exceeds step (b) by 2, 3, 4, 5, 6, 7, 8, 9, 10, 11, 12, 13, 14, 15, 16, 17, 18, 19, or 20 or more cycles.

In some embodiments, the set of tail primers comprises a first tail primer and a second tail primer. In some embodiments, the first tail primer is complementary to the common forward tail and the second tail primer is complementary to the common reverse tail.

In some embodiments, the first tail primer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the first tail primer is greater than 40 nucleotides in length. In some embodiments, the first tail primer is about 10 to 40 nucleotides, or about 15-35 nucleotides, or about 20-30 nucleotides in length.

In some embodiments, the second tail primer is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length. In some embodiments, the second tail primer is greater than 40 nucleotides in length. In some embodiments, the second tail primer is about 10 to 40 nucleotides, or about 15-35 nucleotides, or about 20-30 nucleotides in length.

The concentration of tail primers (forward and reverse tail primers) is high compared to the concentration of inner primers, and sometimes compared to the outer primers as well, such that the tail primers make the most product compared to the outer and inner primers. In some embodiments, the concentration of the first tail primer is 0.01 to 1.0 µM. In some embodiments, the concentration of the first tail primer is 0.05 to 0.5 µM. In some embodiments, the concentration of the first tail primer is 0.01, 0.05, 0.10, 0.15, 0.20, 0.25, 0.30, 0.35, 0.40, 0.45, 0.50, or 1.0 µM.

In some embodiments, the concentration of the second tail primer is 0.01 to 1.0 µM. In some embodiments, the concentration of the second tail primer is 0.05 to 0.5 µM. In some embodiments, the concentration of the second tail primer is 0.01, 0.05, 0.10, 0.15, 0.20, 0.25, 0.30, 0.35, 0.40, 0.45, 0.50, or 1.0 µM.

As detailed in the Summary section above and as is made clear in FIG. 1, 3, or 7, in some embodiments, the ratio of concentration of the inner primers to the concentration of tail multiplexed primers is 2.5:100, 2.5:200, 2.5:300, 2.5:400, 2.5:500, 2.5:600, 2.5:700, 2.5:800, 2.5:900, 2.5:1000, 2.5:1100, 2.5:1200, 2.5:1300, 2.5:1400, 2.5:1500, 2.5:1600, 2.5:1700, 2.5:1800, 2.5:1900, 2.5:2000, 2.5:2500, 2.5:3000, 2.5:4000, 2.5:4500, or 2.5:5000. In some embodiments, the ratio of concentration of the tail primers to the concentration of inner multiplexed primers is 2.5:100-2.5-5:000. In some embodiments, the ratio of concentration of the tail primers to the concentration of inner multiplexed primers is 2.5:500-2.5:1500.

In some embodiments, the ratio of concentration of the tail primers to the concentration of inner multiplexed primers is 2.5-10,000 (e.g., 2.5-10,000, 5-10,000, 5-1,000, 5-200, 5:100, 5-10, 10-100, 10-1,000, 100-1,000, or 1,000-10,000). For example, the concentration of tail primers may be 0.1-1 µM (e.g., 0.1-0.5, 0.1-0.2, 0.2-1, 0.3-1, 0.4-0.8, or 0.5-1 µM) and the concentration of inner multiplexed primers may be 0.0001-0.01 µM (e.g., 0.0001-0.01, or 0.001-0.01 µM).

As detailed in the Summary section above and as is made clear in FIG. 1, 3, or 7, in some embodiments, the ratio of the concentration of the outer primer to the concentration of the inner multiplexed primers is 0.5:10, 0.5:20, 0.5:30, 0.5:40, 0.5:50, 0.5:60, 0.5:70, 0.5:80, 0.5:90, 0.5:100, 0.5:120, 0.5:140, 0.5:160, 0.5:180, 0.5:200, 0.5:220, 0.5:240, 0.5:260, 0.5:280, 0.5:300, 0.5:320, 0.5:340, 0.5:360, 0.5:380, 0.5:400, 0.5:450, 0.5:500, 0.5:550, 0.5:600, 0.5:700, 0.5:800, 0.5:900, or 0.5:1000. In some embodiments, the ratio of the concentration of the tail primer to the concentration of the outer multiplexed primers is 0.5:10-0.5:1000. In some embodiments, the ratio of the concentration of the tail primer to the concentration of the outer multiplexed primers is 0.5:70-0.5:150.

In some embodiments, the ratio of concentration of the tail primers to the concentration of outer multiplexed primers is 0.5-200 (e.g., 0.5-200, 0.5-50, 1-20, 5-200, 5-100, 5-50, 10-200, 10-50, or 50-200). For example, the concentration of tail primers may be 0.1-1 µM (e.g., 0.1-0.5, 0.1-0.2, 0.2-1, 0.3-1, 0.4-0.8, or 0.5-1 µM) and the concentration of outer multiplexed primers may be 0.01-0.2 µM (e.g., 0.01-0.2, or 0.02-0.1 µM).

Hot Start Primers

In some embodiments, a pair of primer (e.g., outer primers, inner primers, or tail primers) is a pair of hot start primers. Hot start primers contain a thermolabile chemical modification that allows hot start activation in PCR, for example, in some embodiments, the primers may have a 4-oxo-tetradecyl (OXT) phosphotriester groups introduced at the 3'-terminal phosphodiester linkages.

In some embodiments, the set of inner multiplexed primers are hot start primers and the set of inner multiplexed primers are activated by subjecting the provided contents in the single reaction vessel to an activation temperature after subjecting the provided contents in the single reaction vessel to an amplification condition which favors the annealing of the set of outer multiplexed primers to the DNA (e.g., after step (b)). In some embodiments, the set of tail primers are hot start primers and the set of tail primers are activated by subjecting the provided contents in the single reaction vessel to an activation temperature after subjecting the provided contents in the single reaction vessel to an amplification condition which favors annealing of the set of inner multiplexed primers (e.g., after step (c)). In some embodiments, the amplification reaction further comprises primers for sequencing adaptor addition and the primers for sequencing adaptor addition are hot start primers.

In some embodiments, the activation temperature of the hot start primers is 85° C., 86° C., 87° C., 88° C., 89° C., 90° C., 91° C., 92° C., 93° C., 94° C., 95° C., 96° C., 97° C., 98° C., 99° C., 100° C., or greater, e.g., 90° C.-95° C.

In some embodiments, the hot start primers are activated after being subjected to an activation temperature for 1, 2, 3, 4, 5, 10, 15, 20, 25, 30, 35, 40, 45, 50, or 55 seconds, or 1, 2, 3, 4, 5, 6, 7, 8, 9, 10, 11, 12, 13, 14, or 15 or more minutes. In some embodiments, the hot start primers are activated after being subjected to an activation temperature for 5 seconds to 5 minutes. In some embodiments, the hot start primers are activated after being subjected to an activation temperature for 2 minutes to 10 minutes.

PCR

In some embodiments, amplification can be performed using a polymerase chain reaction (PCR). As used herein, PCR can refer to a reaction for the in vitro amplification of specific DNA sequences by the simultaneous primer extension of complementary strands of DNA.

The temperature of the reaction solutions may be sequentially cycled between a denaturing state, an annealing state, and an extension state for a predetermined number of cycles. The actual times and temperatures can be enzyme, primer, and target dependent.

For any given reaction, denaturing states can range in certain embodiments from about 75° C. to about 100° C. The annealing temperature and time can influence the specificity and efficiency of primer binding to a particular locus within a target nucleic acid and may be important for particular PCR reactions.

As is described herein, for any given reaction, annealing states can range in certain embodiments from about 20° C. to about 75° C.

Extension temperature and time may impact the allele product yield and are understood to be an inherent property of the enzyme under study. For a given enzyme, extension states can range in certain embodiments from about 60° C. to about 75° C.

In any of the foregoing embodiments, any DNA or RNA polymerase (enzyme that catalyzes polymerization of nucleotides into a nucleic acid strand) may be utilized, including thermostable polymerases and reverse transcriptases (RTases). Examples include *Bacillus stearothermophilus* pol I, *Thermus aquaticus* (Taq) pol I, *Pyrccoccus furiosus* (Pfu), *Pyrococcus woesei* (Pwo), *Thermus flavus* (Tfl), *Thermus thermophilus* (Tth), *Thermus litoris* (Tli) and *Thermotoga maritime* (Tma). These enzymes, modified versions of these enzymes, and combination of enzymes, are commercially available from vendors including Roche, Invitrogen, Qiagen, Stratagene, and Applied Biosystems. Representative enzymes include PHUSION® (New England Biolabs, Ipswich, Mass.), Hot MasterTaq™ (Eppendorf), PHUSION® Mpx (Finnzymes), PyroStart® (Fermentas), KOD (EMD Biosciences), Z-Taq (TAKARA), and CS3AC/LA (KlenTaq, University City, Mo.).

Salts and amplification buffers include those familiar to those skilled in the art, including those comprising $MgCl_2$, and Tris-HCl and KCl, respectively. Amplification buffers may contain additives such as surfactants, dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphosphate (dCTP), deoxyguanosine triphosphate (dGTP), and deoxythymidine triphosphate (dTTP), and are also added to a reaction adequate amount for amplification of the target nucleic acid.

Mutant Enrichment

Mutation enrichment technologies, e.g., COLD-PCR and NaME-PrO, enhance mutation-containing DNA of rare alleles prior to sequencing, thus enabling rapid and efficient sequencing where the result can be obtained with very few sequence reads.

In some embodiments, the methods described herein comprise enriching mutant alleles of the target nucleic acids relative to wild-type alleles of the target nucleic acids. In some embodiments, the methods comprise enriching mutant alleles of the target nucleic acids relative to wild-type alleles of the target nucleic acids before subjecting the provided contents in the single reaction vessel to an amplification reactions described herein. In some embodiments, the methods comprise enriching mutant alleles of the target nucleic acids relative to wild-type alleles of the target nucleic acids after subjecting the provided contents in the single reaction vessel to an amplification condition under which the set of tail primers anneal (e.g., after step (d)). In some embodiments, the methods comprise enriching mutant alleles of the target nucleic acids relative to wild-type alleles of the target nucleic acids while subjecting the provided contents in the single reaction vessel to an amplification condition under which the set of tail primers anneal (e.g., during, or nested within step (d)).

Several methods of enriching mutant target sequence relative to wild-type target sequence are known in the art. Non-limiting examples of mutation enrichment methods include Nuclease-assisted Minor-allele Enrichment using Probe Overlap (NaME-PrO), Coamplification at Lower Denaturation temperature-PCR (COLD-PCR), Improved and Complete Enrichment COLD-PCR (ice-COLD-PCR), Temperature-Tolerant ice-COLD-PCR (TT-ice-COLD-PCR), toehold PCR, and Differential Strand Separation at Critical Temperature (DiSSECT).

NaMe or NaMe-PrO methods are described in PCT/US2016/039167, which is incorporated by reference in its entirety. Use of NaMe-PrO in the methods described herein is shown in FIG. 7. NaMe-PrO is shown as the first step, before the amplification methods described herein. A non-limiting example of a NaMe-PrO protocol includes:

(a) preparing an amplification reaction mixture comprising the double-stranded mutant and wild-type target nucleic acids, a thermostable double strand-specific nuclease (DSN), PCR amplification components, and a pair of oligonucleotide probes, one of which is complementary to the wild-type nucleic acid top strand and the other is complementary to the wild-type nucleic acid bottom strand, wherein the probes may overlap each other by 10-15 probes such that the overlap coincides with the target region or be non-overlapping and contiguous;

(b) subjecting the reaction mixture to a denaturing temperature to permit denaturation of the wild-type nucleic acid and the mutant target nucleic acid;

(c) reducing the temperature to permit hybridization of the probes to their corresponding sequences on the wild-type and mutant target nucleic acids thereby forming complementary wild-type-probe duplexes, wherein the DSN cleaves the complementary wild-type-probe duplexes but not the partially complementary target mutant-probe duplexes; and (d) subjecting the reaction mixture to an amplification condition thereby enriching the uncleaved mutant target nucleic acid relative to the cleaved wild-type nucleic acid.

In some embodiments, an overlap of NaMe-PrO probes coincides with one or more mutations. In some embodiments, NaMe-PrO probes have a 3'-terminal polymerase block. In some embodiments, the probes are complementary to SNPs near target mutations.

In some embodiments, NaMe-PrO is performed before the amplification reactions described herein, e.g., before providing the double-stranded DNA (e.g., genomic DNA, or cDNA), the set of outer multiplexed primers, the set of inner multiplexed primers and the set of tail primers in the single reaction vessel. In some embodiments, NaMe-PrO is performed after the amplification reactions described herein.

In some embodiments, NaMe or NaMe-PrO is then followed by amplification of remaining mutant and wild-type target nucleic acids according to the methods described herein.

In some embodiments, NaMe-PrO with or without amplification results in mutation enrichment relative to wild-type target nucleic acids of 1-200-fold (e.g., 1-150-, 5-100- or 10-100-fold) compared to the unenriched sample. In some embodiments, NaMe-PrO with or without amplification results in mutation enrichment relative to wild-type target nucleic acids of more than 200-fold (e.g., 250-fold or 300-fold).

In some embodiments, a form of COLD-PCR (e.g., ice-COLD-PCR, TT-ice-COLD-PCR or oscillating COLD-PCR) is used to enrich mutant target nucleic acids relative to wild-type target nucleic acids. Methods of COLD-PCR and oscillating COLD-PCR are described in WO 2009/017784, which is incorporated by reference herein in its entirety. Use of COLD-PCR in the methods described herein is shown at least in FIG. 3.

In the first step of FIG. 3 (e.g., step (a)), the contents of the reaction, including the three sets of primers, the genomic DNA, and the COLD-PCR reference sequence are provided to the reaction vessel. In the second step of FIG. 3 (e.g., step (b)), the set of outer multiplexed primers, which are complementary to the genomic DNA, anneal to the genomic DNA and amplify a segment of the genomic DNA. In the third step of FIG. 3 (e.g., step (c)), the set of inner multiplexed primers anneal to the amplified genomic DNA and a shorter segment of genomic DNA is amplified having tail segments attached to the ends. In the fourth step of FIG. 3 (e.g., step (d)), the tail primers anneal to the tail segments on the amplification product from step (c) and the genomic DNA portion having tail segments at the end is further amplified. COLD-PCR occurs during the fourth step of FIG. 3, with the annealing temperature being the critical temperature for COLD-PCR (as described below). The reference sequence, which is perfectly complementary to the wild type sequence, binds to the wild type sequence but not the mutant sequence, allowing preferential amplification of the mutant sequence. The concentration of the reference is kept low, e.g., 1-10 nM, so that it does not appreciably bind the amplification product in the first amplification step.

In some embodiments, the concentration of the reference sequence is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 nM.

A non-limiting example of a COLD-PCR protocol includes:

(a) denaturing the double-stranded mutant and wild-type target nucleic acids by subjecting the double-stranded target mutant and wild-type nucleic acids to a first denaturing temperature that is above the melting temperature of the wild-type nucleic acid;

(b) forming a target mutant/wild-type strand duplex;

(c) denaturing said mutant/wild-type strand duplex by subjecting the nucleic acid sample to a critical temperature (Tc) that is below the Tm of the wild-type nucleic acids;

(d) annealing a primer pair to the mutant and wild-type target nucleic acid strands; and (e) extending said primer pair so as to enrich said mutant target sequence relative to said wild-type strand.

In some embodiments, COLD-PCR is performed while subjecting the provided contents in the single reaction vessel to an amplification condition under which the set of tail primers anneal (e.g., during step (d)).

In some embodiments, COLD-PCR is performed after subjecting the provided contents in the single reaction vessel to an amplification condition under which the set of tail primers anneal (e.g., after step (d)). In some embodiments, COLD-PCR is performed for 1-50 cycles (e.g., 1-40, 2-30, 5-25, 8-20 or 5-10 cycles) to enrich mutant target nucleic acid relative to wild-type target nucleic acid.

In some embodiments, COLD-PCR is performed in the same tube as the amplification methods described herein. In some embodiments, the reagents for the enrichment of mutant alleles of the target nucleic acids relative to wild-type alleles of the target nucleic acids are provided with the double-stranded DNA (e.g., genomic DNA, or cDNA), the set of outer multiplexed primers, the set of inner multiplexed primers and the set of tail primers in the single reaction vessel.

If the above example of COLD-PCR were to be adapted for oscillating COLD-PCR, steps (b) and (c) would be repeated. In some embodiments of oscillating COLD-PCR, forming a target mutant/wild-type strand duplex and denaturing said mutant/wild-type strand duplex, is repeated 1-29 times (e.g., 1-19 or 2-9 times).

Methods of ice-COLD-PCR and TT-COLD-PCR are described in WO 2012/135664, which is incorporated by reference herein in its entirety. A non-limiting example of a ice-COLD-PCR protocol includes:

(a) exposing the mutant and wild-type target nucleic acids to a reference sequence that is complementary the target sequence;

(b) denaturing the double-stranded target mutant and wild-type nucleic acids by subjecting the double-stranded mutant and wild-type target nucleic acids to a first denaturing temperature that is above the melting temperature of the wild-type nucleic acid;

(c) forming a target mutant/reference strand and target wild-type/reference strand duplexes;

(d) denaturing said mutant/reference strand duplex by subjecting the nucleic acid sample to a critical temperature (Tc) that is below the Tm of the wild-type/reference duplex;

(e) annealing a primer pair to the mutant and wild-type target nucleic acid strands; and (f) extending said primer pair so as to enrich said mutant target sequence relative to said wild-type target nucleic acid.

A non-limiting example of a TT-ice-COLD-PCR (also known as temperature independent (TI)-ice-COLD-PCR) protocol includes:

(a) exposing the mutant and wild-type target nucleic acids to a reference sequence that is complementary the target sequence;

(b) denaturing the double-stranded target mutant and wild-type target nucleic acids by subjecting the double-stranded target mutant and wild-type nucleic acids to a denaturing temperature that is above the melting temperature of the wild-type nucleic acid;

(c) forming a target mutant/reference strand and target wild-type/reference strand duplexes;

(d) denaturing said mutant/reference strand duplex by subjecting the nucleic acid sample to a first critical temperature (Tc) that is below the Tm of the wild-type/reference duplex;

(e) annealing a primer pair to the mutant and wild-type target nucleic acid strands;

(f) extending said primer pair so as to enrich said mutant target nucleic acid relative to said wild-type target nucleic acid; and (f) repeating steps (d) to (f) at least once at a second Tc which is above the first Tc.

In some embodiments, any form of COLD-PCR (as described above) with or without amplification results in mutation enrichment relative to wild-type target nucleic acids of 1-200-fold (e.g., 1-150-, 5-100- or 10-100-fold) compared to the unenriched sample. In some embodiments, any form of COLD-PCR with or without amplification results in mutation enrichment relative to wild-type target nucleic acids of more than 200-fold (e.g., 250-fold or 300-fold) compared to the unenriched sample.

In some embodiments, DiSSECT is used to enrich mutant target nucleic acids relative to wild-type target nucleic acids. DiSSECT is a method that enriches unknown mutations of targeted DNA sequences purely based on thermal denaturation of DNA duplexes without the need for enzymatic reactions. Methods of DiSSECT are described Guha et al. (Nucleic Acids Research, 2012, 1-9), which is incorporated herein by reference in its entirety. A non-limiting example of a DiSSECT protocol includes:

(a) allowing mutant and wildtype target nucleic acids to bind to complementary probes which are immobilized to beads, wherein the probes resemble the wild-type nucleic acids;

(b) denaturing the target mutant/probe duplex by subjecting the nucleic acid sample to a critical temperature such that the wild-type/probe duplex does not denature;

(c) collecting the eluate from the beads; and (d) repeating at least once (a)-(c) using beads on which the probes are unbound to any nucleic acid.

In some embodiments, DiSSECT is performed for 1-20 cycles (e.g., 1-18, 2-6, 2-4, 2-10 or 5-15 cycles). In some embodiments, DiSSECT results in mutation enrichment relative to wild-type target nucleic acids of 1-600-fold (e.g., 100-fold, 200-fold, 300-fold, 400-fold, 500-fold or 600-fold) compared to the unenriched sample.

Toehold PCR is described by Wu et al. Nat Methods. 2015 December; 12(12):1191-6, which is incorporated herein in its entirety.

The term 'mutant' refers to a nucleotide change (i.e., a single or multiple nucleotide substitution, deletion, insertion, or methylation, or alteration in the number of polynucleotide repeats) in a nucleic acid sequence. A nucleic acid which bears a mutation has a nucleic acid sequence (mutant allele) that is different in sequence from that of the corresponding wild-type sequence. Herein, the term "mutant target nucleic acid" is used interchangeably with "mutant alleles of target nucleic acid." Similarly, the term "wild-type target nucleic acid" is used interchangeably with "wild-type alleles of target nucleic acid." The mutant alleles can contain between 1 and 500 nucleotide sequence changes. A mutant allele may have 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400 or 500 nucleotide sequence changes compared to a corresponding wild-type allele. Typically, a mutant allele will contain between 1 and 10 nucleotide sequence changes, and more typically between 1 and 5 nucleotide sequence changes. The mutant allele will have 50%, 60%, 70%, 80%, 85%, 90%, 91%, 92%, 93%, 94%, 95%, 96%, 97%, 98%, 99% or more homology to the wild-type allele. Generally, the mutant allele will be obtained from diseased tissues or cells and is associated with a disease state.

'Allele' refers to alternative forms of a gene, portion thereof or non-coding region of DNA that occupy the same locus or position on homologous chromosomes that have at least one difference in the nucleotide sequence. The term allele can be used to describe DNA from any organism including but not limited to bacteria, viruses, fungi, protozoa, molds, yeasts, plants, humans, non-humans, animals, and archaebacteria. The alleles may be found in a single cell (e.g., two alleles, one inherited from the father and one from the mother) or within a population of cells (e.g., a wild-type allele from normal tissue and a somatic mutant allele from diseased tissue). Alleles will generally share 50%, 60%, 70%, 80%, 85%, 90%, 91%, 92%, 93%, 94%, 95%, 96%, 97%, 98%, 99% or more homology to each other.

Quantitation

Low-level tumor somatic DNA mutations can have profound implications for development of metastasis, prognosis, choice of treatment, follow-up or early cancer detection. Unless effectively detected, these low-level mutations can misinform patient management decisions or become missed opportunities for personalized medicine. Next generation sequencing (NGS) technologies reveal prevalent somatic mutations, yet they 'lose steam' when it comes to detecting low-level DNA mutations in tumors with clonal heterogeneity, or in bodily fluids during 'liquid biopsy', and their integration with clinical practice is not straightforward. For mutations at an abundance of ~2-5% or less, NGS generates false positives ('noise') independent of sequencing depth and hinders personalized clinical decisions based on mutational profiling. Recent enhancements employing single molecule barcoding (or Unique Identifiers, UIDs) enable NGS to overcome noise and detect 'ultra-rare mutations'. (Kinde et al., Proc Natl Acad Sci USA 2011, 108:9530-5; Schmitt et al., Proc Natl Acad Sci USA 2012; Gregory et al., Nucleic Acids Res 2016, 44:e22; Jee et al., Nature 2016). Furthermore, the use of molecular barcodes (UIDs) at the initial stages of sample preparation (i.e. before application of mutation enrichment via COLD-PCR or NaME-PrO) allows for strict quantification of original mutation abundance following mutation enrichment.

One exemplary method of quantifying mutant DNA using barcodes in conjunction with the amplification methods described herein is shown in FIG. 12. In step 1, the DNA (e.g., genomic DNA, or cDNA) is fragmented. In step 2, barcodes, e.g., unique identifiers, with upstream common sequence tags, are ligated onto both ends of the fragmented DNA. The box outlines the amplification methods described herein. In the first amplification reaction, the fragmented DNA is amplified with an outer forward primer complimentary to the common sequence tag (e.g., a tail) and a gene-specific outer reverse primer. This generates a DNA fragment with a barcode and tail on one end. In the second amplification reaction, the product of the first amplification reaction is amplified with an inner forward primer complimentary to the common sequence tag and an inner reverse primer that has a gene-specific portion that is nested relative to the outer reverse primer, and that further comprises a tail. This generates a DNA molecule with a tail and barcode on one end and a tail on the other end. In the third amplification reaction, the product of the second amplification reaction is amplified with a forward tail primer that is complimentary to the common sequence tag and a reverse tail primer that is complementary to the tail of the inner reverse primer. This generates a DNA molecule with a tail and barcode on one end and a tail on the other end. The mutant allele can either be enriched by performing COLD-PCR in conjunction with the amplification reaction, as is described above, or by performing NaME-PrO enrichment after the amplification reaction, followed by 10 cycles of PCR using the tail primers.

The term "barcode" as used herein refers to a unique sequence of nucleotides that allows identification of the nucleic acid of which the barcode is a part. Barcoding a DNA fragment is a process by which the DNA fragment is uniquely tagged with one or more short identifying sequences. In some embodiments, it is desired for each DNA fragment in a sample to have a barcode that is unique from barcodes on any other DNA fragment in the sample. In some embodiments, each DNA fragment in a sample comprises one unique barcode. In some embodiments, each DNA fragment in as sample comprises two barcodes that are unique from each other and unique from any other barcode that is attached to any other DNA fragment in the sample. Such uniqueness of barcodes in a sample of DNA fragments can be accomplished, for example, by optimizing the length of each barcode (i.e., the number of nucleotides in each barcode) and/or the ratio of unique barcodes to DNA fragments during barcoding (i.e., attaching barcodes to DNA fragments).

Barcodes can be any appropriate length. In some embodiments, the length of each barcode used to barcode DNA fragments in a sample is 6-20 bp long (e.g., 8-18 bp, 8-14 bp, 10-16 bp or 12-14 bp). In some embodiments, the length of each barcode used to barcode DNA fragments in a sample is 14 bp long.

Barcodes can be attached to DNA fragments in any appropriate ratio. In some embodiments, the ratio of unique barcodes to DNA fragments during barcoding is $10^6$-$10^{10}$ (e.g., $10^6$, $10^7$, $10^8$, $10^9$, $10^{10}$) unique barcodes to 100 ng of DNA (or $3\times10^4$ allelic copies).

Methods of attaching barcodes to nucleic acids are known in the art. Various publications provide descriptions of barcoding technology. For example, Wong and Moqtaderi (Curr Protoc Mol Biol. 2013; Chapter 7:Unit 7.11) describe a barcoding protocol for the preparation of up to 96 ChIP samples for multiplex sequencing in a single flow cell lane on the Illumina platform; and Stahlberg et al. (Nucleic Acids Res. 2016 Jun. 20; 44) describe a PCR-based barcoding method, both of which are incorporated herein by reference in their entirety. The following patents that also describe DNA barcoding methods are also incorporated herein by reference in their entirety: U.S. Pat. Nos. 8,691,509, 8,268,564 and US application 20120220494A1.

In some embodiments, double-stranded barcodes are attached to a double-stranded DNA fragment by ligation. In some embodiments, double-stranded DNA fragments are barcoded using PCR technique employing primers that comprise unique barcodes.

In some embodiments, the barcodes are attached to the DNA (e.g., genomic DNA, or cDNA) with a common sequence tag prior to the amplification methods described herein. As used herein, the term, "common sequence tag" refers to a nucleotide sequence that is common to all the DNA fragments in a sample, e.g., a sample of genomic fragmented DNA. A common tag enables processing of all the DNA fragments in a sample. For example, primers complementary to a common tag in a sample may be used to amplify all DNA fragments in a sample, regardless of whether a DNA fragment contains target nucleic acid (e.g., mutant target nucleic acid or wild-type target nucleic acid) or non-target nucleic acid.

In some embodiments, the common sequence tag comprises the forward or reverse tail sequence. In some embodiments, the outer forward primer comprises a common sequence tag. In some embodiments, the outer reverse primer comprises a common sequence tag. In some embodiments, the inner forward primer comprises a common sequence tag. In some embodiments, the inner reverse primer comprises a common sequence tag. In some embodiments, the forward tail primer comprises a common sequence tag. In some embodiments, the reverse tail primer comprises a common sequence tag.

For any one of the methods disclosed herein, a sample of double-stranded DNA (e.g., genomic DNA, or cDNA) may comprise double-stranded DNA fragments, wherein each terminus of the DNA fragments is attached to a unique double-stranded barcode and a double-stranded common sequence tag, wherein the common sequence tag is located upstream of the unique barcode. By being located "upstream" of the unique tag, it is meant that the common tag is located 5' relative to the unique tag if the unique barcode, common tag and DNA fragment sequence are read from 5' to 3'.

Common sequence tags can be any appropriate length. In some embodiments, a common tag is 16-40 bp long (e.g., 16-40, 18-36, 20-32, 22-30 or 24-28 bp long). In some embodiments, a common tag is 18 nucleotides long (i.e. an 18-mer). It is to be understood that a the terms "nucleotide" and 'base pair (bp)" are used interchangeably herein.

In some embodiments, a unique barcode and a common tag are attached to each end of a double-stranded DNA fragment at the same time using the same method. In some embodiments, a barcode and a common tag are attached to each end of a double-stranded DNA fragment by ligation.

In some embodiments, a unique barcode and common tag are attached to a terminus of a DNA fragment by starting from a single-stranded barcode, synthesizing the opposite strand of the single-stranded barcode using an extension reaction to form a double stranded barcode, and the ligating and end of the double-stranded DNA (e.g., genomic DNA, or cDNA) fragment to the end of the barcode.

In some embodiments, a barcode and a common tag are attached to each end of a double-stranded DNA fragment by using multiplexed-PCR. In such embodiments, PCR using oligonucleotide primers are used, wherein each oligonucleotide primer comprises a common tag portion, a unique barcode portion and a target-specific portion. The target-specific portion enables attachment of the oligonucleotide primer to anneal to DNA fragments.

In some embodiments, the methods disclosed herein require DNA (e.g., genomic DNA, or cDNA) to be in fragmented form In some embodiments, DNA in a sample collected from a subject is already fragmented. For example, a sample of cell-free DNA or DNA circulating in blood is fragmented when collected. In some embodiments, DNA from samples of the urine of a subject is fragmented. In some embodiments, DNA collected from bodily fluid or tissue sample of a subject is not fragmented and needs to be fragmented. In some embodiments, a sample of DNA is fragmented but it is desired to fragment it further to make smaller fragments. Various techniques to fragment double-stranded DNA are known in the art. In some embodiments, DNA is sheared physically (e.g., using acoustic shearing using a Covaris instrument, sonication using a Bioruptor or hydrodynamic shearing using a Hydroshear instrument). In some methods, double-stranded DNA is sheared enzymatically using any DNAase type of enzyme that digests DNA randomly (e.g., a Shearase, DNAse1 or a transposase). In some embodiments, double-stranded DNA is fragmented by chemical fragmentation (e.g., by exposing the DNA to be fragmented to heat and divalent metal cation. Depending on the method of DNA fragmentation, DNA fragments may be subjected to enzymatic end-repairing to obtain blunt ends.

In some embodiments of any one of the methods disclosed herein, a double-stranded DNA fragment is 20-400 bp long (e.g., 10-400, 40-200, 50-150 or 50-100 bp long).

In any of the methods disclosed herein, obtaining a measure of total unique barcodes in a sample may be accomplished using DNA sequencing methods. Several sequencing methods and protocols for sample preparation for these methods are well-established in the art. Indeed, one of the advantages of the methods disclosed herein is that they are compatible with established methods of sample preparation for sequencing methods used in the field. Examples of methods of sequencing include SANGER sequencing, MiSeq sequencing, massively parallel signature sequencing (MPSS), polony sequencing, 454 sequencing, Illumina (or Solexa) sequencing, SoLiD sequencing, Ion Torrent semiconductor sequencing, single molecule real time (SMRT) sequencing, and nanopore sequencing. The following publications describe various sequencing options and are incorporated herein by reference in their entirely: Goodwin et al. (Coming of age: ten years of next-generation sequencing technologies, Nature Reviews Genetics 17, 333-351 (2016)), Heather and Chain (The sequence of sequencers: The history of sequencing DNA, Genomics, 107: 1-8 (2016)), and Moorthie et al. (Review of massively parallel DNA sequencing technologies, Hugo J. 2011 December; 5(1-4): 1-12).

EXAMPLES

Example 1: Combined Multiplexed-PCR Reactions that Provide Target Enrichment and Amplification Along with Mutation Enrichment The processes of target enrichment and mutation enrichment can be combined in a single tube reaction ('all-in-one') to combine the sequential steps of selecting DNA targets for sequencing from DNA (e.g., genomic DNA, or cDNA), and addition of the Illumina sequencing adaptor. This highly efficient, all-in-one reaction includes in a single tube:
1. The DNA to be interrogated (genomic DNA, circulating DNA, saliva DNA or DNA from any other source human, animal of plant).
2. A first set of multiplexed, outer primers that target the DNA sites of interest
3. A second set of inner multiplexed primers that are nested to the outer primers. These primers comprise a gene-specific portion and common forward and reverse oligonucleotide 'tails' towards the 5'end. The tails optionally comprise 20-30 bp of the 3'-end portion of the Illumina adaptors that enable binding to the Illumina flow-cell during sequencing. Or similarly, to enable binding to the Qiagen sequencing adaptors; or binding to the Ion Torrent sequencing cell; or adaptors to the sequencing cell of any other sequencing system.
4. A forward and a reverse oligonucleotide 'tail', without the gene-specific portion, which can be used as a primer to amplify all sequences carrying the same tail on their 5'end.
5. PCR amplification components: DNA polymerase, dNTP, PCR buffer to enable PCR amplification The all-in-one reaction approach is described in FIG. 1. The multi-stage single tube PCR reaction can optionally start with a low number of cycles (e.g., 10 cycles) to produce an initial amplification of selected targets from genomic DNA using an annealing temperature (Ta) that fits the outer multiplexed primers. Similarly, the 'tail' primers will not participate in the reaction as there is no corresponding binding site (for example, the tails may have the sequence corresponding to the 3'-end of the Ilumina sequencing adaptor, which has no homology to common human sequences).

Following the first 10 PCR cycles, there will be enough target built-up from the outer multiplexed primers that the anchor-tail primers can bind to it and generate nested PCR product carrying the sequence of the 'tails' on the 5'end. The annealing temperature can also be adjusted to fit optimally the annealing temperature of the anchor-tail oligonucleotides. Because of their very low concentration (0.001-0.01 µM), and different Ta, these oligonucleotides do not produce significant amount of product directly from the original genomic DNA during the initial 10 cycles. Similarly, the 'tail' primers do not participate in the reaction during the first 10 cycles as there is no corresponding binding site in genomic DNA (for example, the tails may have the sequence corresponding to the 3'-end of the Ilumina sequencing adaptor, which has no homology to common human sequences).

However, once the pre-amplification reaction builds enough product following the initial 10 cycles, then anchor-tail oligonucleotides, which are nested to the outer oligonucleotides, start generating products containing the Tails (tail 1=forward; tail 2=reverse). The tails are at high concentration (0.1-0.2 µM) such that, in subsequent cycles, they take over the amplification for the remaining 20-30 cycles of the reaction.

In this way, the 'all-in-one reaction' enables highly specific selection of DNA targets (in view of two nested PCR reactions), and incorporation of a tail sequence that corresponds to the Illumina sequencing adaptor. Finally, to prepare the product for sequencing, an additional few cycles of PCR using the Illumina adaptor containing individual 'sample barcodes' can be used and the product is processed for sequencing.

In FIG. 1 described above, it is also note-worthy that (optionally) to separate the action of the first set of (outer) multiplexed primers from the action of the second set (nested) anchor-tail primers within the multi-stage PCR reaction, a substantially different annealing temperature Ta can be used for these two sets of primers. For example, the Tm of the multiplexed outer primers can be 65° C., so that a Ta of 60-65° C. would be appropriate for these primers; while the Tm of the anchor-tail primers can be 55° C. so that a Ta of 50-55° C. would be appropriate. In this example, during the first 10 cycles of PCR using Ta=65° C. mainly the outer primers would generate product from genomic DNA. And by changing the Ta to 50° C. after the first 10 cycles one would activate the nested multiplexed anchor-MB-tail primers to generate highly specific, nested products using the amplicons generated by the outer primers.

Hot Start Primers

As an additional way to separate the action of the various primers within the multi-stage PCR reaction, one may include 'hot start primers' (available from Trilink Technologies, Inc.), whose action is only activated when the temperature stays at high levels (e.g., 90-95° C. for 2-10 min). In this way the thermo-activatable primers will not interfere at earlier steps of the 'all-in-one' reaction, and will only become activated at a selected time point. For example, the anchor-tail primers can be designed as 'hot' start' primers using a 3-end modification provided by Trilink Inc. Thus, after the first 10 cycles of PCR, the temperature can be elevated for a few minutes to 95° C. to activate the second set of primers. In the same way, a 'hot start' tail can be used to regulate when the tail primer can be activated in the reaction. Thus, one can arrange that the tail is activated after the initial 14 cycles of PCR, upon which both the outer and the inner primers have applied their actions and produced the required template for the tail primers. Finally, one may also include host start versions of the Illumina adaptors shown at the bottom of FIG. 1, in the multi-stage PCR reaction from the start. The Illumina adaptors will only become thermo-activated after all the other primers included in the reaction complete their intended action. In this way, there will not be a need for an additional PCR to attach the Illumina adaptors at the end.

Figure 2:
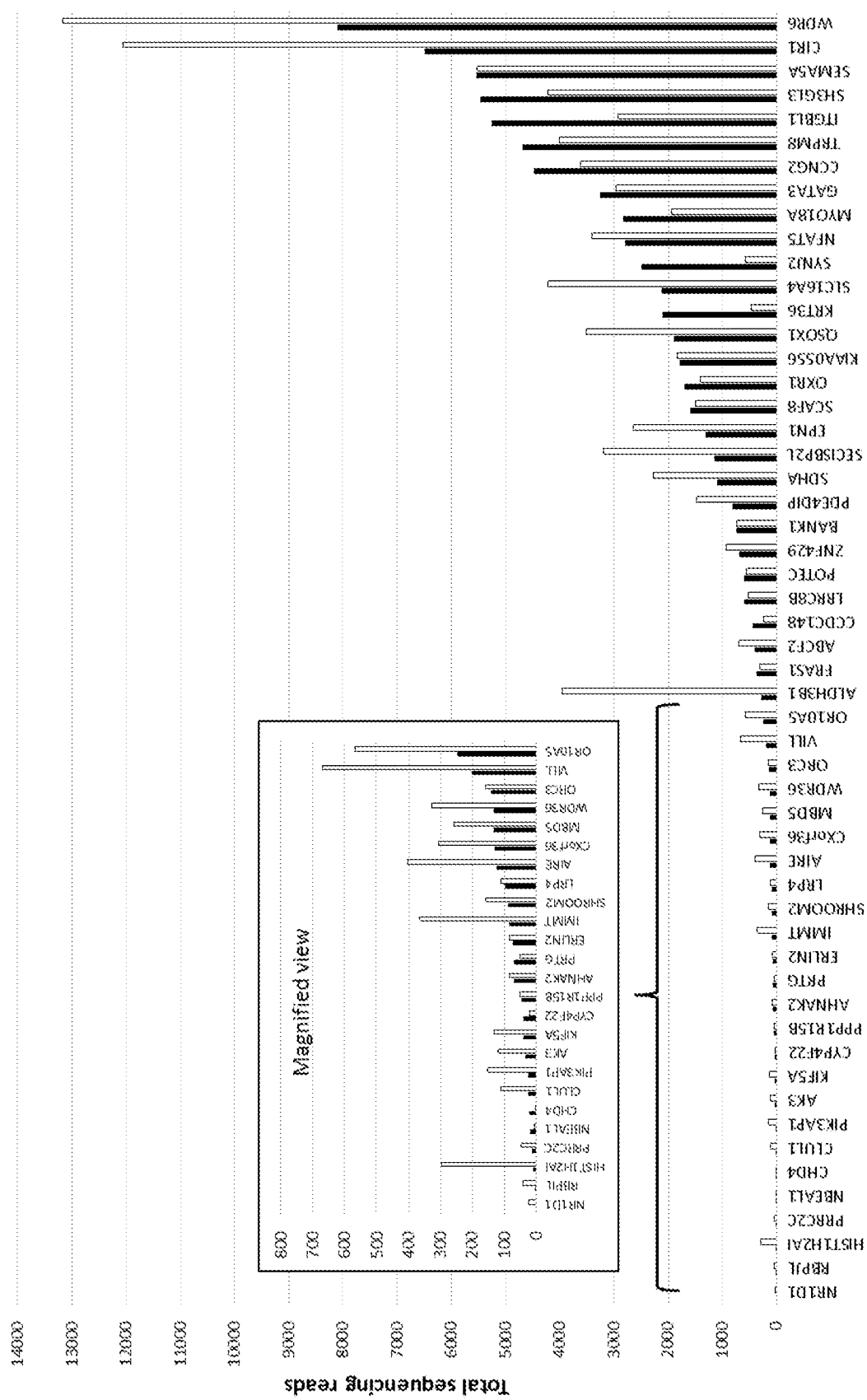
FIG. 2 shows a comparison of the single-tube multi-step PCR approach (in black) with the established, multi-step PCR sample preparation method (in white) for 54 DNA targets amplified from genomic cfDNA simultaneously. The number of Miseq reads (total counts) follows the same general trends for both approaches, thus validating the single tube approach.

An example of the all-in-one reaction for multiplexed PCR with 54 target genes co-amplified from circulating DNA is shown on FIG. 2. The protocol described in FIG. 1 was applied for the 54 gene targets shown on the x-axis, while the y axis shown the number of sequencing reads obtained for each of the targets tested. The all-in-one protocol in FIG. 1 (in BLACK) is compared to a conventional step-by-step multiplexed PCR approach, during which the outer primers are used for a first standard multiplexed PCR; this is then followed with sample purification and dilution and a second, nested PCR (in WHITE). Both approaches show the same general trends, thus validating the single step approach.

All-in-One, Single Tube PCR Reaction Incorporating Mutation Enrichment Via COLD-PCR The methods described above may optionally also incorporate COLD-PCR cycling during the last part of the multi-stage PCR reaction, thereby providing selective amplification of mutation-containing sequences in addition to highly specific target selection. This approach is shown in FIG. 3, in combination with ICE-COLD-PCR. In this approach, a blocker Reference Sequence is included in the reaction mix from the beginning, and the approach shown in FIG. 1 is now modified to incorporate ICE-COLD-PCR cycling for the last 10-15 cycles of the reaction.

Figure 5A:
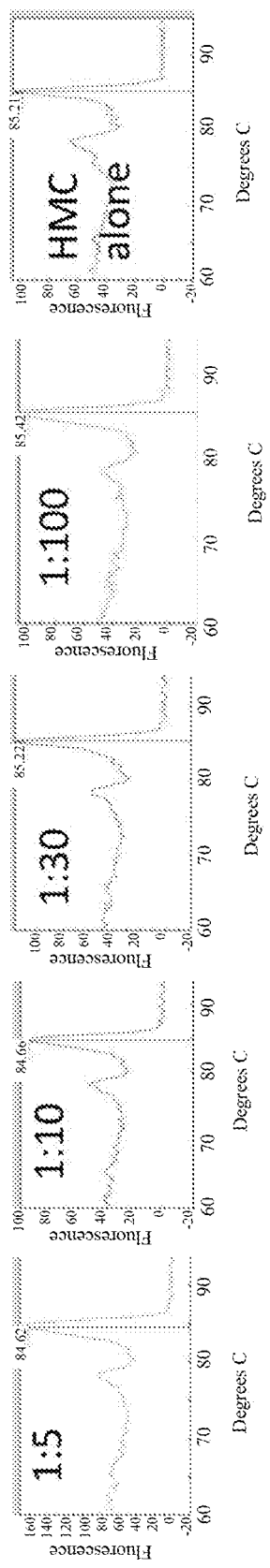
FIG. 5A shows a melting curve analysis of the single-tube multiplexed all-in-one ICE-COLD-PCR reaction for BRAF and KRAS.
Figure 5B:
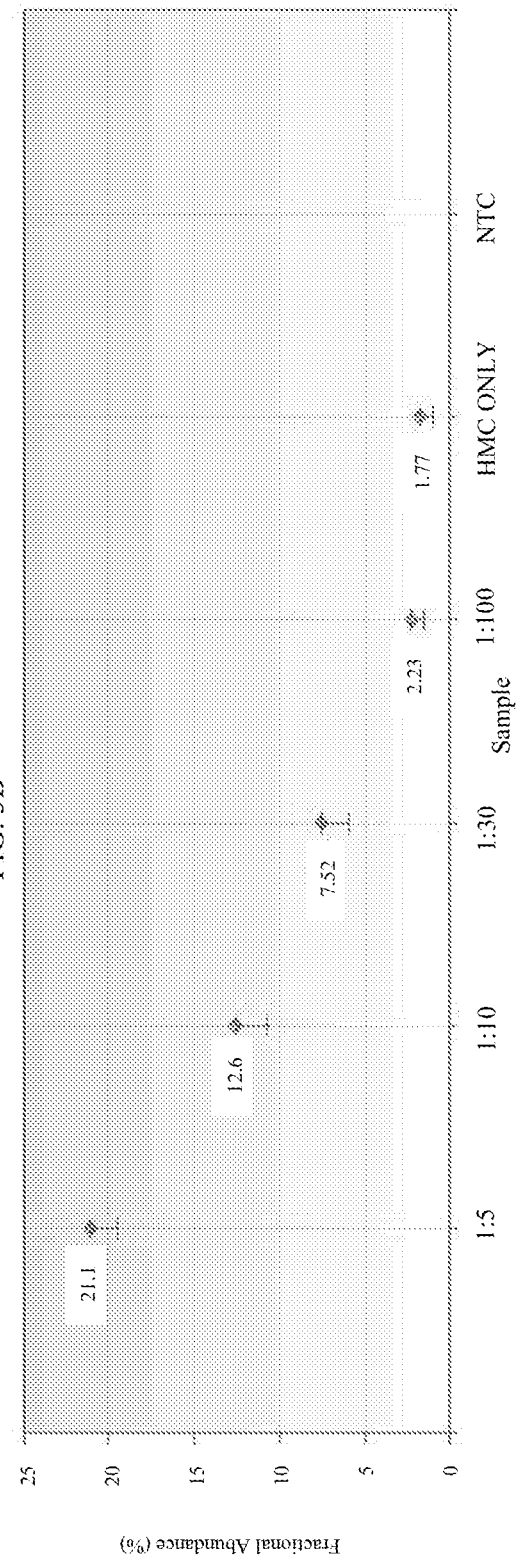
FIGS. 5B and 5C show digital PCR performed for KRAS that demonstrates mutation enrichment during the single tube reaction. A serial mutation dilution experiment was performed, where KRAS and BRAF mutations were diluted at known, decreasing amounts. The resulting mutation enrichment is inferred by the fractional abundance detected via digital PCR (left axis). For example, the 1:10 sample has an original mutation abundance of about 0.35%, which becomes 12.6% after the single-tube reaction. This indicates an approximate 36-fold mutation enrichment.
Figure 5C:
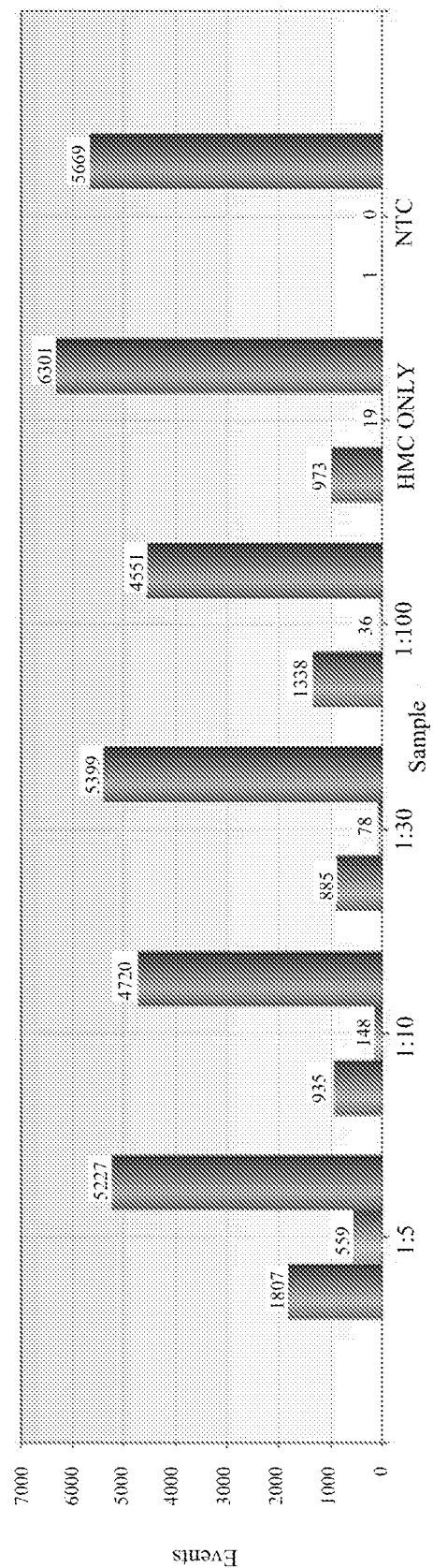
Figure 6A:
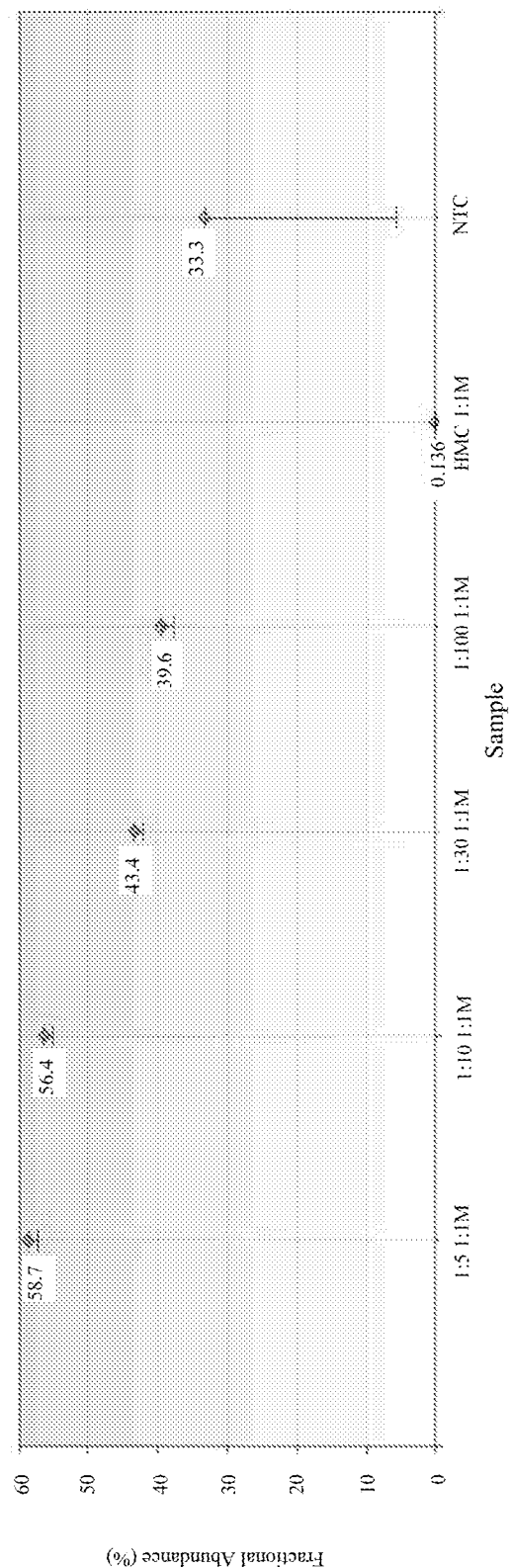
FIGS. 6A-6B are similar to FIGS. 5B and 5C, but digital PCR was performed here for BRAF in the same serial dilutions to demonstrate mutation enrichment during the single tube reaction for the second target, BRAF. A serial mutation dilution experiment was performed, where KRAS and BRAF mutations were diluted at known, decreasing amounts. The resulting mutation enrichment is inferred by the fractional abundance detected via digital PCR (left axis). For example, the 1:10 sample has an original mutation abundance of about 2%, which becomes 56.4% after the single-tube reaction. This indicates an approximate 27-fold mutation enrichment.
Figure 6B:
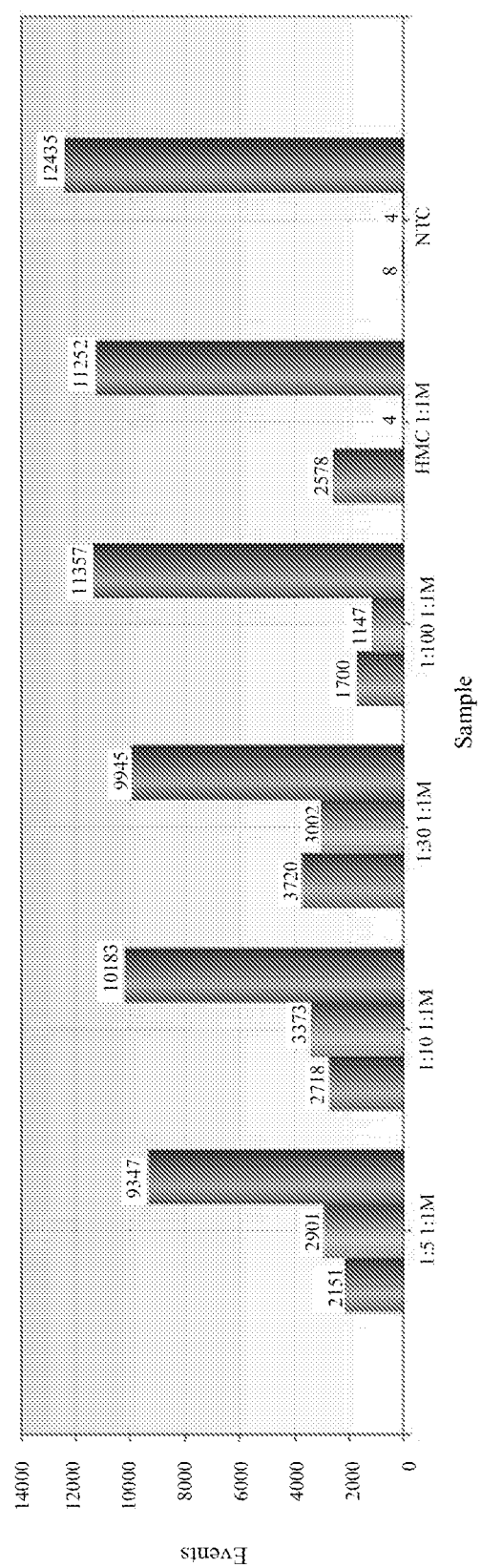

An example of an all-in-one, single step reaction incorporating mutation enrichment for two targets, KRAS and BRAF, is shown in FIG. 4 (PCR cycling conditions), FIG. 5 (results of testing KRAS mutation enrichment in serial mutation dilutions via ddPCR) and FIG. 6 (results of testing BRAF mutation enrichment in serial mutation dilutions via ddPCR). The data show that strong mutation enrichment occurs simultaneously with highly specific target selection in a single reaction from genomic DNA.

All-in-One, Single Tube PCR Reaction Incorporating Mutation Enrichment Via NaME-PrO The methods described above may optionally also incorporate NaME-PrO reaction during the first step of the process, followed by a multi-stage all-in-one PCR reaction, thereby providing selective amplification of mutation-containing sequences in addition to highly specific target selection, FIG. 7. NaME-PrO is applied directly on genomic DNA as described[5].

All-in-One, Single Tube PCR Reaction Incorporating Molecular Barcodes Plus Optional Mutation Enrichment Via NaME-PrO (OR Via COLD-PCR)

Figure 8:
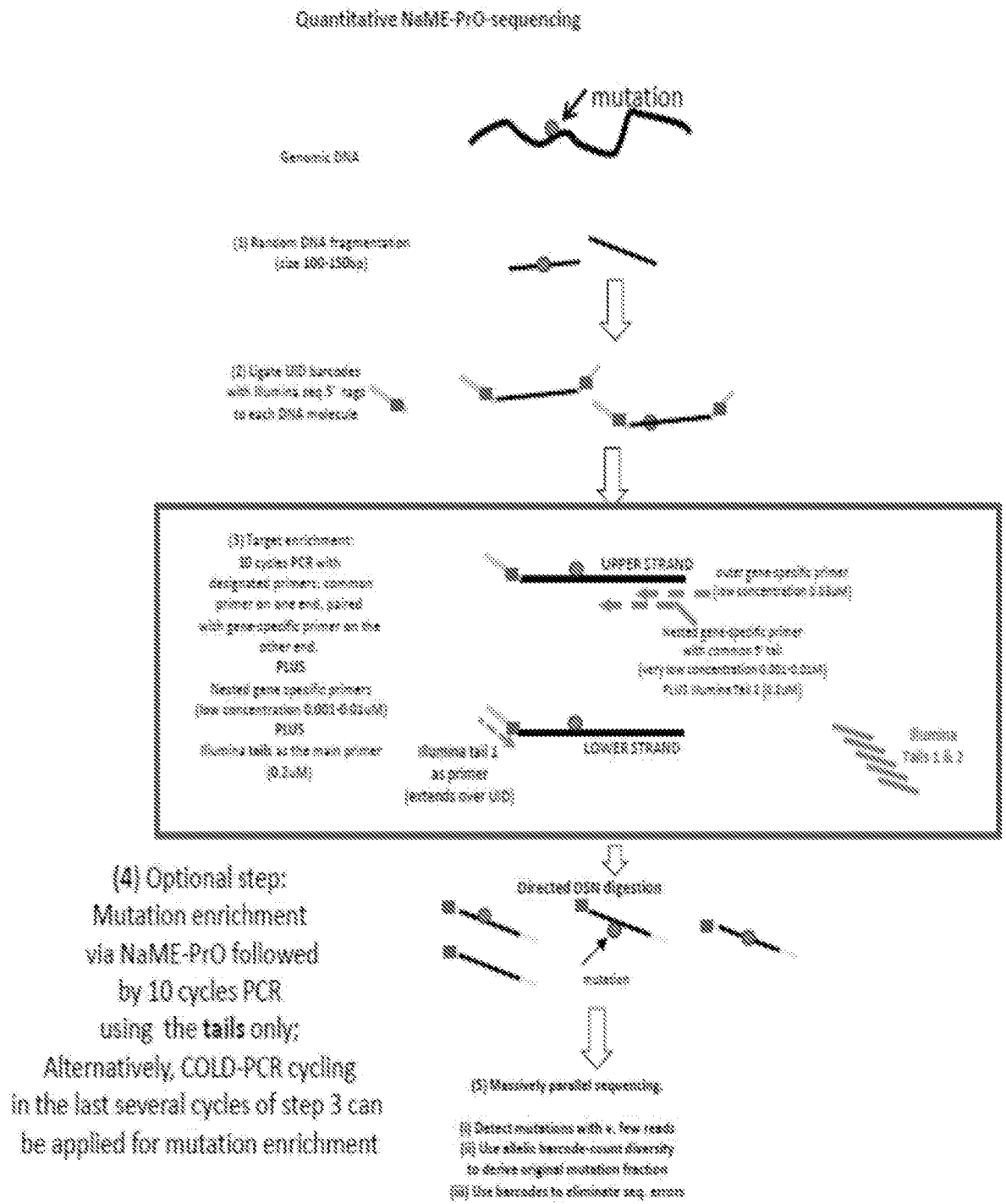
FIG. 8 shows combined outer gene-specific primer, plus nested gene-specific primer PCR plus 'tail' primer for highly specific target selection that includes ligated UIDs (molecular barcode) on the other end. This can be optionally combined with NaME-PrO or COLD-PCR for mutation enrichment. Attachment of molecular barcodes (UID) at step 1 using ligation, is followed by an 'all-in-one' target enrichment using gene-specific primers only on one end of each DNA target, plus the generic linker ligated in the first step. This approach ensures that the selected DNA targets will always contain the molecular barcode.

The methods can also be combined to enable an all-in-one reaction that retains the molecular barcode UID on one end of the targets, as described in FIG. 8. Enrichment can be provided either via COLD-PCR protocol at the last several cycles of the all-in-one reaction described in step 3 OR by an additional NAME-PRO step plus amplification/library construction. The general methods described in previous sections can be applied here too, in order to achieve all-in-one target selection, mutation enrichment and molecular barcode retention so that the UID can be sequenced along with the selected targets.

LITERATURE CITED

[1] Kinde I, Wu J, Papadopoulos N, Kinzler K W, Vogelstein B: Detection and quantification of rare mutations with massively parallel sequencing. Proc Natl Acad Sci USA 2011, 108:9530-5.

[2] Schmitt M W, Kennedy S R, Salk J J, Fox E J, Hiatt J B, Loeb L A: Detection of ultra-rare mutations by next-generation sequencing. Proc Natl Acad Sci USA 2012.

[3] Gregory M T, Bertout J A, Ericson N G, Taylor S D, Mukherjee R, Robins H S, Drescher C W, Bielas J H: Targeted single molecule mutation detection with massively parallel sequencing. Nucleic Acids Res 2016, 44:e22.

[4] Jee J, Rasouly A, Shamovsky I, Akivis Y, S R S, Mishra B, Nudler E: Rates and mechanisms of bacterial mutagenesis from maximum-depth sequencing. Nature 2016.

[5] Song C, Liu Y, Fontana R, Makrigiorgos A, Mamon H, Kulke M H, Makrigiorgos G M: Elimination of unaltered DNA in mixed clinical samples via nuclease-assisted minor-allele enrichment. Nucleic Acids Res 2016.

[6] Shagin D A, Rebrikov D V, Kozhemyako V B, Altshuler I M, Shcheglov A S, Zhulidov P A, Bogdanova E A, Staroverov D B, Rasskazov V A, Lukyanov S: A novel method for SNP detection using a new duplex-specific nuclease from crab hepatopancreas. Genome research 2002, 12:1935-42.

[7] Gnirke A, Melnikov A, Maguire J, Rogov P, LeProust E M, Brockman W, Fennell T, Giannoukos G, Fisher S, Russ C, Gabriel S, Jaffe D B, Lander E S, Nusbaum C: Solution hybrid selection with ultra-long oligonucleotides for massively parallel targeted sequencing. Nat Biotechnol 2009, 27:182-9.

[8] Mertes F, Elsharawy A, Sauer S, van Helvoort J M, van der Zaag P J, Franke A, Nilsson M, Lehrach H, Brookes A J: Targeted enrichment of genomic DNA regions for next-generation sequencing. Briefings in functional genomics 2011, 10:374-86.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A method of selecting and amplifying DNA targets in a single reaction vessel, the method comprising the following steps:

(a) providing in the single reaction vessel:
 a sample of double-stranded DNA,
 a set of outer multiplexed primers comprising an outer forward primer and an outer reverse primer, wherein each of the outer forward and reverse primers complement target nucleic acids on the DNA, and wherein the concentration of the outer multiplexed primers is 0.01-0.2 µM,
 a set of inner multiplexed primers comprising an inner forward primer and an inner reverse primer, wherein each of the inner forward and reverse primers comprises a target-specific anchor on its 3' end, and the inner forward primer comprises a common forward tail on its 5' end and the inner reverse primer comprises a common reverse tail on its 5' end, wherein the common forward tail is different from the common reverse tail, and wherein the concentration of the inner multiplexed primers is 0.001-0.04 µM,
 a set of tail primers comprising of a first tail primer and a second tail primer, wherein the first tail primer is complementary to the common forward tail and the second tail primer is complementary to the common reverse tail, and wherein the concentration of the tail primers is 0.1-1 µM,
 wherein the outer multiplexed primers have an annealing temperature of 60-65° C., and the inner multiplexed primers have an annealing temperature of 50-55° C., or wherein the outer multiplexed primers have an annealing temperature of 58-62° C., and the inner multiplexed primers have an annealing temperature of 66-70° C.;

(b) subjecting the provided contents in the single reaction vessel to an amplification condition which is carried out for 8-12 cycles and favors the annealing of the set of outer multiplexed primers to the DNA;

(c) subjecting the provided contents in the single reaction vessel to an amplification condition which is carried out for 2-6 cycles and favors annealing of the set of inner multiplexed primers to amplified products of step (b); and (d) subjecting the provided contents in the single reaction vessel to an amplification condition which is carried out for 10-30 cycles and under which the set of tail primers anneal to the amplified products of step (c).

2. The method of claim 1, further providing in the single reaction vessel a DNA polymerase, dNTPs and an amplification buffer.

3. The method of claim 1, wherein the annealing temperature of the inner multiplexed primers is 5-15° C. lower or 5-10° C. higher than the annealing temperature of the outer multiplexed primers.

4. The method of claim 1, wherein the annealing temperature of the tail primers is 3-20° C. lower or higher than the annealing temperature of the inner multiplexed primers.

5. The method of claim 4, wherein the annealing temperature of the tail primers is 60-70° C.

6. The method of claim 1, wherein the inner multiplexed primers are hot start primers, activated by subjecting the provided contents in the single reaction vessel to an activation temperature after the completion of step (b) or step (c).

7. The method of claim 6, wherein the activation temperature is 90-95° C., and wherein the provided contents in the single reaction vessel is subjected to the activation temperature for 5 seconds to 5 minutes.

8. The method of claim 1, wherein the ratio of the concentration of outer multiplexed primers to the concentration of inner multiplexed primers is 0.25-2000, the ratio of the concentration of the tail primers to the concentration of inner multiplexed primers is 5-200, or the ratio of the concentration of the tail primer to the concentration of the outer multiplexed primers is 1-20.

9. The method of claim 1, wherein the number of amplification cycles in step (d) exceeds the number of amplification cycles in step (b).

10. The method of claim 1, wherein the tail primers further comprise 20-30 bp of a 3'end portion of a sequencing adapter.

11. The method of claim 1, wherein the inner forward and inner reverse primers each further comprise, between the target-specific anchor and the common forward or reverse tails, a central portion that is a unique barcode.

12. The method of claim 11, wherein the inner multiplexed primers are provided such that the ratio of DNA to unique barcodes is $10^7$-$10^9$ unique barcodes to 100 ng DNA.

13. The method of claim 1, further comprising enriching mutant alleles of the target nucleic acids relative to wild-type alleles of the target nucleic acids after the completion of step (d).

14. The method of claim 13, wherein the enriching the mutant alleles of the target regions relative to wild-type alleles of the target nucleic acids comprises subjecting the provided contents in the single reaction vessel after completion of step (d) to Nuclease-assisted Minor-allele Enrichment using Probe Overlap (NaME-PrO), Coamplification at Lower Denaturation temperature-PCR (COLD-PCR), Improved and Complete Enrichment COLD-PCR (ice-COLD-PCR), Temperature-Tolerant-ice-COLD-PCR (TT-ice-COLD-PCR), toehold PCR, or Differential Strand Separation at Critical Temperature (DiSSECT).

15. The method of claim 1, wherein step (d) comprises one or more of the following: Coamplification at Lower Denaturation temperature-PCR (COLD-PCR), Improved and Complete Enrichment COLD-PCR (ice-COLD-PCR), Temperature-Tolerant-ice-COLD-PCR (TT-ice-COLD-PCR), and toehold PCR.

16. A reaction mixture comprising
a set of outer multiplexed primers that complement target nucleic acids on DNA,
a set of outer multiplexed primers at a concentration of 0.01-0.2 µM comprising an outer forward primer and an outer reverse primer, wherein each of the outer forward and reverse primers complement target nucleic acids on the DNA,
a set of inner multiplexed primers at a concentration of 0.001-0.04 µM comprising an inner forward primer and an inner reverse primer, wherein each of the inner forward and reverse primers comprises a target-specific anchor on its 3' end, and the inner forward primer comprises a common forward tail on its 5' end and the inner reverse primer comprises a common reverse tail on its 5' end, wherein the common forward tail is different from the common reverse tail,
a set of tail primers at a concentration of 0.1-1 µM comprising of a first tail primer and a second tail primer, wherein the first tail primer is complementary to the common forward tail and the second tail primer is complementary to the common reverse tail,
wherein the outer multiplexed primers have an annealing temperature of 60-65° C., and the inner multiplexed primers have an annealing temperature of 50-55° C., or wherein the outer multiplexed primers have an annealing temperature of 58-62° C., and the inner multiplexed primers have an annealing temperature of 66-70° C.

17. A reaction mixture comprising
a set of outer multiplexed primers at a concentration of 0.01-0.2 µM comprising an outer forward primer and an outer reverse primer, wherein (i) the outer forward primer complements a common tag and the outer reverse primer complements target nucleic acids on DNA, or (ii) the outer reverse primer complements a common tag and the outer forward primer complements target nucleic acids on DNA,
a set of inner multiplexed primers at a concentration of 0.001-0.04 µM comprising an inner forward primer and an inner reverse primer, wherein (H) the inner forward primer is complementary to the common tag, which comprises a common forward tail, and wherein the inner reverse primer comprises a target-specific anchor on its 3' end and a common reverse tail on its 5' end, or (ii) the inner reverse primer is complementary to the common tag, which comprises a common reverse tail, and wherein the inner forward primer comprises a target-specific anchor on its 3' end and a common forward tail on its 5' end,
wherein the common forward tail is different from the common reverse tail, and
a set of tail primers at a concentration of 0.1-1 µM comprising of a first tail primer and a second tail primer, wherein the first tail primer is complementary to the common forward tail and the second tail primer is complementary to the common reverse tail,
wherein the outer multiplexed primers have an annealing temperature of 60-65° C., and the inner multiplexed primers have an annealing temperature of 50-55° C., or wherein the outer multiplexed primers have an annealing temperature of 58-62° C., and the inner multiplexed primers have an annealing temperature of 66-70° C.

\* \* \* \* \*